(12) United States Patent
Nozaki

(10) Patent No.: US 9,463,339 B2
(45) Date of Patent: Oct. 11, 2016

(54) CLEANING FILTER, AIR CLEANING DEVICE USING SAME, AND AIR CLEANING MAINTENANCE SYSTEM

(76) Inventor: Atsuo Nozaki, Koriyama (JP)

( * ) Notice: Subject to any disclaimer, the term of this patent is extended or adjusted under 35 U.S.C. 154(b) by 0 days.

(21) Appl. No.: 13/505,957

(22) PCT Filed: Nov. 4, 2010

(86) PCT No.: PCT/JP2010/069634
§ 371 (c)(1),
(2), (4) Date: May 3, 2012

(87) PCT Pub. No.: WO2011/055762
PCT Pub. Date: May 12, 2011

(65) Prior Publication Data
US 2012/0219462 A1     Aug. 30, 2012

(30) Foreign Application Priority Data

Nov. 4, 2009   (JP) ................................ 2009-252542
Dec. 4, 2009   (JP) ................................ 2009-276092

(51) Int. Cl.
*A62B 7/08*     (2006.01)
*A62B 23/02*    (2006.01)
(Continued)

(52) U.S. Cl.
CPC .............. *A62B 23/025* (2013.01); *A62B 7/10* (2013.01); *A62B 9/02* (2013.01); *A62B 18/006* (2013.01); *A62B 18/02* (2013.01); *A62B 18/084* (2013.01);
(Continued)

(58) Field of Classification Search
CPC .......................... A62B 23/025; B01D 53/0462
USPC ......................................................... 422/122
See application file for complete search history.

(56) References Cited

U.S. PATENT DOCUMENTS 6,878,177 B2 *   4/2005   Lohr et al. ................... 55/385.2
2005/0160911 A1 *   7/2005   Friday et al. ................... 96/134
(Continued)

FOREIGN PATENT DOCUMENTS

JP         10-202046 A       8/1998
JP         2001259330 A  *   9/2001
(Continued)

OTHER PUBLICATIONS

English Translation of Japanese Document No. JP 2001259330A provided by the Japan Platform for Patent Information: Shiga, Akira; Air Cleaner and Household Electric Appliance; Sep. 25, 2001.*

(Continued)

*Primary Examiner* — Kevin Joyner
(74) *Attorney, Agent, or Firm* — Birch, Stewart, Kolasch & Birch, LLP

(57) ABSTRACT

The cleaning filter includes a gas trapping member (6) and a particle trapping member (5). The gas trapping member (6) or the particle trapping member (5) includes: a trapping material (7) for trapping a predetermined contaminant in the air; and a trapping material holding member (8) for holding the trapping material (7) so as to be opposed to the air flow passage (3) with an air permeability ensured. The trapping material holding member (8) is subjected to, when removed from a cleaning apparatus main body (2), a regeneration process for regenerating trapping performance of the trapping material (7) for the predetermined contaminant under a state in which the trapping material holding member (8) holds the trapping material (7).

12 Claims, 28 Drawing Sheets

(51) Int. Cl.
    *B01D 53/04*     (2006.01)
    *A62B 7/10*     (2006.01)
    *A62B 9/02*     (2006.01)
    *A62B 18/02*     (2006.01)
    *A62B 18/08*     (2006.01)
    *A62B 18/10*     (2006.01)
    *A62B 18/00*     (2006.01)
    *E03D 9/052*     (2006.01)
    *F24F 3/16*     (2006.01)
    *B01J 20/34*     (2006.01)

(52) U.S. Cl.
    CPC ........... *A62B 18/10* (2013.01); *B01D 53/0462* (2013.01); *B01J 20/3416* (2013.01); *B01J 20/3483* (2013.01); *E03D 9/052* (2013.01); *F24F 3/16* (2013.01); *A61L 2209/14* (2013.01)

(56) References Cited

U.S. PATENT DOCUMENTS

2005/0229562 A1*   10/2005   Dallas et al. ................... 55/486
2008/0003132 A1*   1/2008   McGee et al. ................... 422/4

FOREIGN PATENT DOCUMENTS

| JP | 2003-293428 A | 10/2003 |
| JP | 2006-22977 A | 1/2006 |
| JP | 2007-136059 A | 6/2007 |

OTHER PUBLICATIONS

International Search Report for PCT/JP2010/069634 dated Jan. 25, 2011.

* cited by examiner

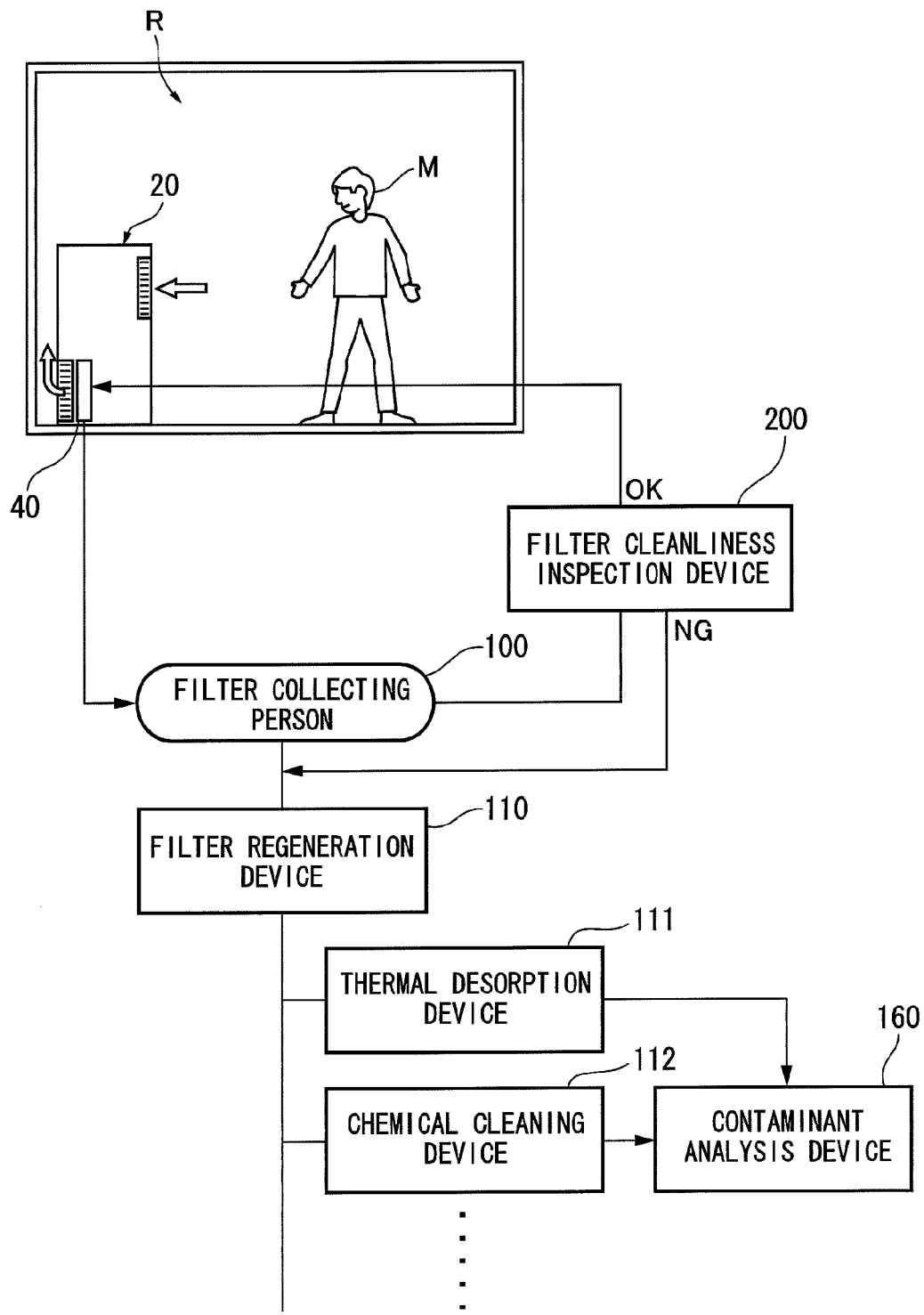

FIG.10A
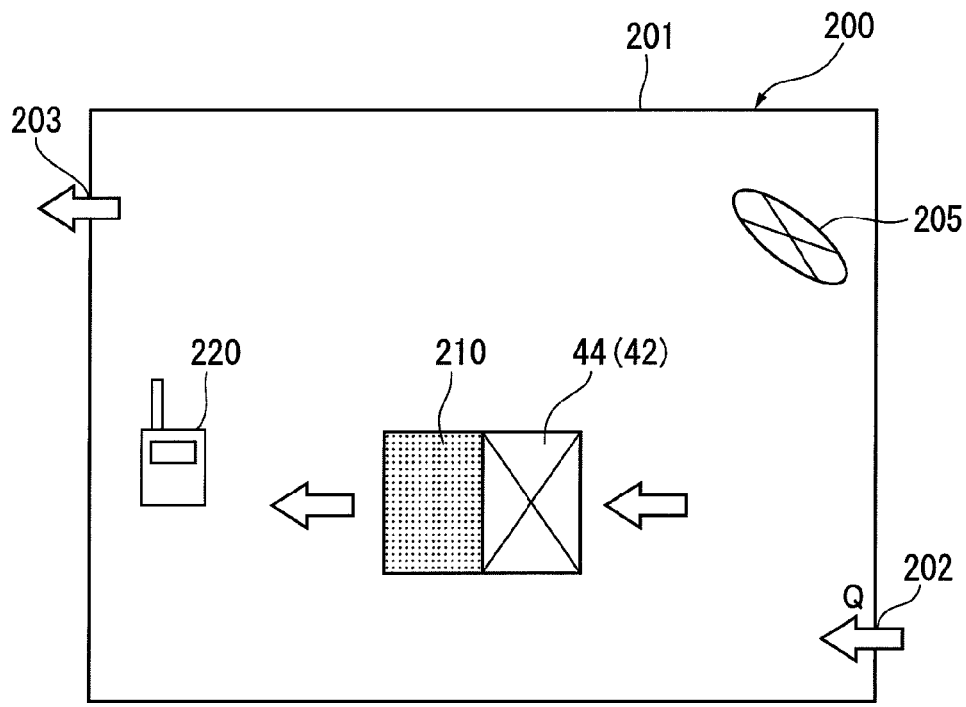
FIG.10B
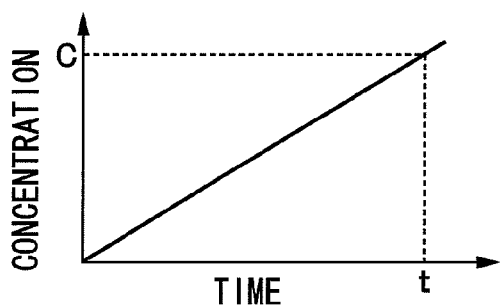
FIG.10C
$$M = \frac{mR(C - C_i e^{-mt})}{1 - e^{-mt}} - QC_0$$
FIG.10D
GENERATION QUANTITY
REFERENCE
$M_1 [\mu g/h] < X_1$
$M_2 [\mu g/h] < X_2$
$M_3 [\mu g/h] < X_3$
⋮

$G_A$: GASEOUS CONTAMINANT
$G_B$: $H_2O$
$G_C$: $CO_2$
$G_D$: DECOMPOSED PRODUCT

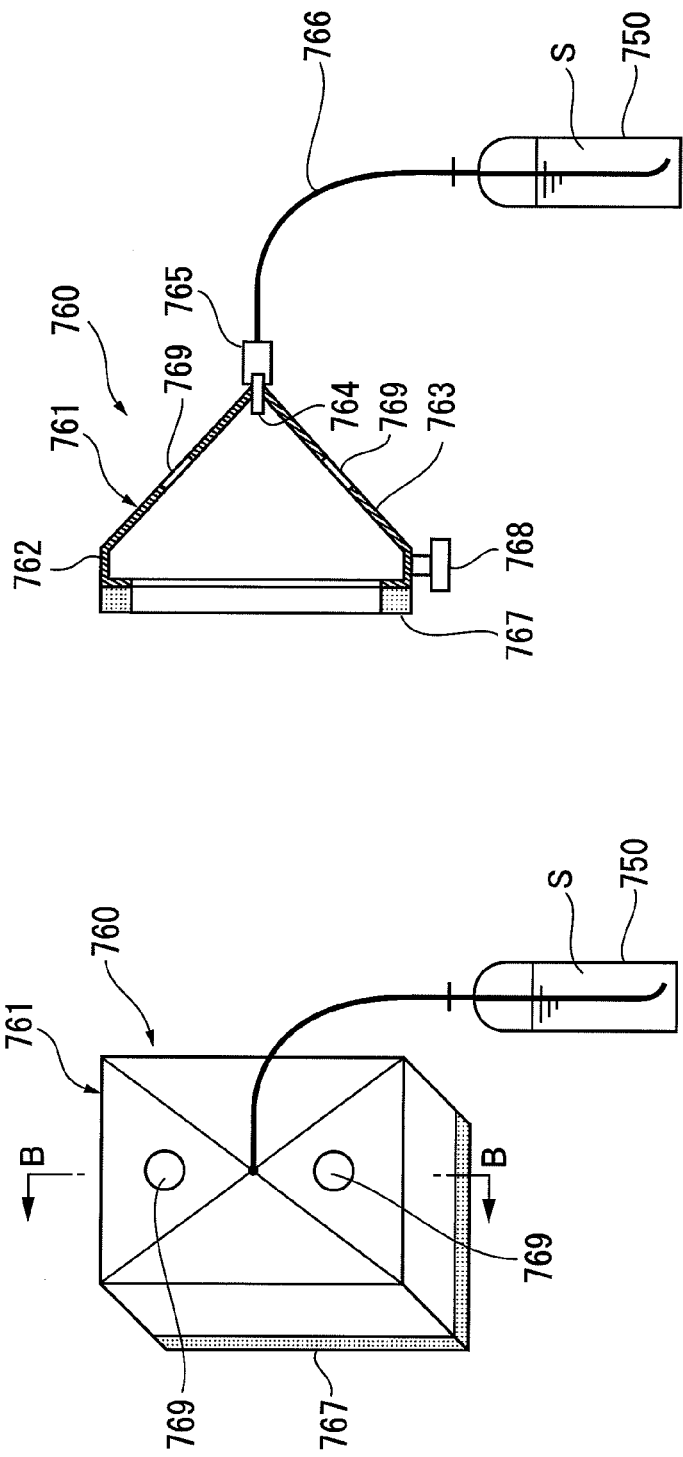

FIG.20
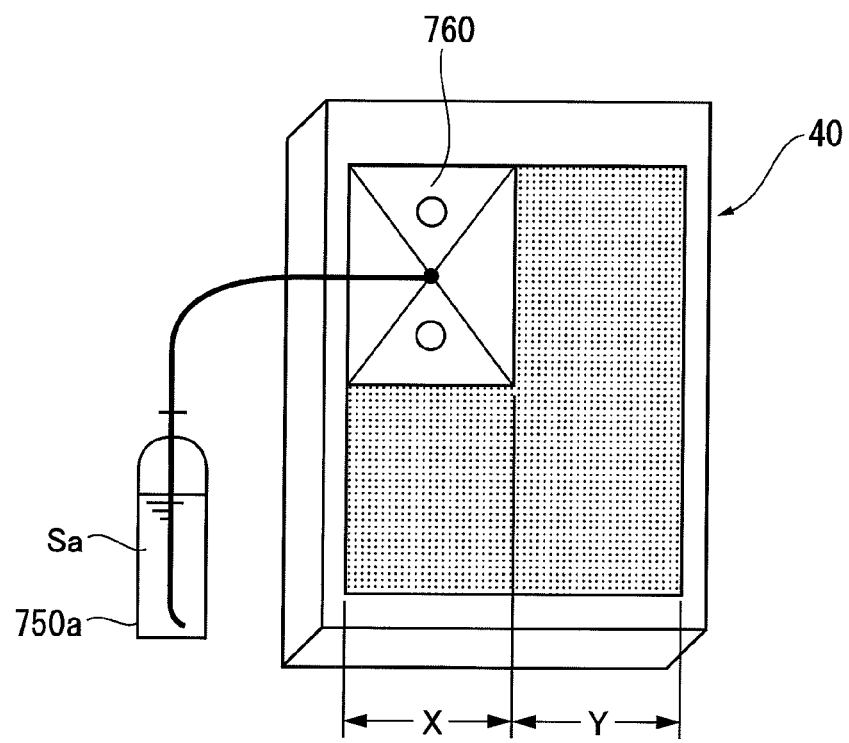
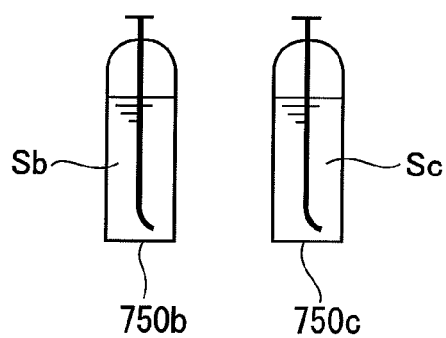

$$\eta = \left(1 - \frac{C_{out}}{C_{in}}\right) \times 100$$

$\eta$ : FORMALDEHYDE REMOVAL RATE [%]
$C_{in}$ : UPSTREAM SIDE GAS CONCENTRATION
$C_{out}$ : DOWNSTREAM SIDE GAS CONCENTRATION

CLEANING FILTER, AIR CLEANING DEVICE USING SAME, AND AIR CLEANING MAINTENANCE SYSTEM

TECHNICAL FIELD

The present invention relates to a cleaning filter to be used in an air cleaning apparatus, and an air cleaning apparatus and air cleaning maintenance system using the cleaning filter.

BACKGROUND ART

Conventionally, as this type of air cleaning apparatus, there has been known a technology for facilitating mounting/removal of a filter unit with respect to a main body of the air cleaning apparatus in order to enable the filter unit to be removed and cleaned (refer to, for example, Patent Literature 1).

CITATION LIST

Patent Literature

PTL 1: JP 2006-22977 A (Best Mode for carrying out the Invention, FIG. 1)

SUMMARY OF INVENTION

Technical Problem

The present invention provides a cleaning filter, and an air cleaning apparatus and air cleaning maintenance system using the cleaning filter, which are capable of trapping gaseous contaminants (odor/chemical substances) and particulate contaminants (dust, microbial particles, allergenic particles, and the like), and of regenerating or recovering trapping performance for predetermined contaminants.

Means for Solving the Problems

First aspect of the invention according to item 1 is a cleaning filter, which is disposed in an air flow passage of a cleaning apparatus main body of an air cleaning apparatus, for cleaning an air passing through the air flow passage, the cleaning filter including: a gas trapping member for trapping a gaseous contaminant; and a particle trapping member for trapping a particulate contaminant, in which at least one of the gas trapping member and the particle trapping member comprises: a trapping material for trapping a predetermined contaminant in the air; and a trapping material holding member, which is removably mounted on the cleaning apparatus main body, for holding the trapping material so as to be opposed to the air flow passage with an air permeability ensured, and in which the trapping material holding member is subjected to, when removed from the cleaning apparatus main body, a regeneration process for regenerating trapping performance of the trapping material for the predetermined contaminant under a state in which the trapping material holding member holds the trapping material.

Second aspect of the invention according to item 2 is a cleaning filter according to item 1, in which the trapping material holding member has a heat resistance, and in which the trapping material having a heat resistance is regenerated by the regeneration process including a thermal desorption process.

Third aspect of the invention according to item 3 is a cleaning filter according to item 1 or 2, in which the trapping material holding member has a heat resistance, and in which the trapping material held by the trapping material holding member is eliminated by the regeneration process including a thermal desorption process.

Fourth aspect of the invention according to item 4 is a cleaning filter according to any one of items 1 to 3, in which the trapping material holding member includes: an outer holding frame having an air permeability; and a plurality of baffle plates contained in the outer holding frame, in which a solid trapping material is filled to be distributed with an air permeability ensured.

Fifth aspect of the invention according to item 5 is a cleaning filter according to item 2 or 3, in which the trapping material holding member of the particle trapping member comprises a plurality of mesh layers each having a different air permeability and made of a material having a heat resistance, the plurality of mesh layers holding an additive as the trapping material.

Sixth aspect of the invention according to item 6 is a cleaning filter according to any one of items 1 to 5, in which the trapping material holding member of the gas trapping member holds the trapping material for trapping a predetermined gaseous contaminant, and further holds a catalyst particle capable of decomposing the predetermined gaseous contaminant, the catalyst particle being provided upstream of the trapping material in an air flowing direction.

Seventh aspect of the invention according to item 7 is a cleaning filter, which is disposed in an air flow passage of a cleaning apparatus main body of an air cleaning apparatus, for cleaning an air passing through the air flow passage, the cleaning filter including: a gas trapping member for trapping a gaseous contaminant; and a particle trapping member for trapping a particulate contaminant, in which at least one of the gas trapping member and the particle trapping member includes: a trapping material for trapping a predetermined contaminant in the air; a trapping material holding member for holding the trapping material so as to be opposed to the air flow passage with an air permeability ensured; and a trapping material supply device for supplying the trapping material to the trapping material holding member so as to recover trapping performance of the trapping material for the predetermined contaminant.

Eighth aspect of the invention according to item 8 is a cleaning filter according to item 7, in which the trapping material holding member is removably mounted on the cleaning apparatus main body, and is subjected to, when removed from the cleaning apparatus main body, a regeneration process for regenerating the trapping performance of the trapping material for the predetermined contaminant under a state in which the trapping material holding member holds the trapping material.

Ninth aspect of the invention according to item 9 is a cleaning filter according to item 7, in which the trapping material holding member has a heat resistance, and is subjected to the regeneration process including a thermal desorption process.

Tenth aspect of the invention according to item 10 is a cleaning filter according to item 7, in which the trapping material supply device selectively supplies the trapping material capable of trapping a predetermined contaminant from among the gaseous contaminant and the particulate contaminant.

Eleventh aspect of the invention according to item 11 is a cleaning filter according to item 7, in which the trapping material supply device comprises a spray tool capable of spraying a liquid trapping material, and in which a spray condition of the spray tool for the liquid trapping material is set so that the liquid trapping material is sprayed in an entire holding region of a predetermined trapping material with respect to the trapping material holding member.

Twelfth aspect of the invention according to item 12 is a cleaning filter according to item 7, in which the trapping material supply device is removably mounted on the trapping material holding member, the trapping material supply device being mounted on the trapping material holding member when supplying the trapping material, and being removed from the trapping material holding member when not supplying the trapping material.

Thirteenth aspect of the invention according to item 13 is a cleaning filter according to item 12, in which the cleaning filter comprises a trapping material holding member having a holding region of the trapping material which is formed into a rectangular shape, and in which the trapping material supply device includes: a spray tool capable of spraying a liquid trapping material; and a spray region restricting member, which is disposed on the spray tool or in a spray path of the liquid trapping material from the spray tool, for restricting a spray region shape of the liquid trapping material into a rectangular shape.

Fourteenth aspect of the invention according to item 14 is a cleaning filter according to item 12, in which the trapping material supply device includes: a spray tool capable of spraying a plurality of kinds of liquid trapping materials; and a trapping material storage container for separately storing the plurality of kinds of liquid trapping materials.

Fifteenth aspect of the invention according to item 15 is an air cleaning apparatus, including: a cleaning apparatus main body in which an air flow passage is formed; and the cleaning filter according to any one of items 1 to 14, the cleaning filter being disposed in the air flow passage of the cleaning apparatus main body.

Sixteenth aspect of the invention according to item 16 is an air cleaning apparatus, including: a cleaning apparatus main body in which an air flow passage is formed; and the cleaning filter according to item 6, the cleaning filter being disposed in the air flow passage of the cleaning apparatus main body, in which the cleaning filter or the cleaning apparatus main body comprises heating means capable of heating the catalyst particle.

Seventeenth aspect of the invention according to item 17 is an air cleaning maintenance system, including: the air cleaning apparatus according to item 15 or 16; and a filter regeneration device for regenerating the cleaning filter removed from the air cleaning apparatus, in which the regenerated cleaning filter is reused.

Advantageous Effects of Invention

According to first aspect of the invention of item 1, gaseous contaminants and particulate contaminants can be trapped, and trapping performance for predetermined contaminants can be regenerated.

According to second aspect of the invention of item 2, the trapping material itself can be regenerated by the thermal desorption process as the regeneration process.

According to third aspect of the invention of item 3, the degraded trapping material held on the trapping material holding member can be eliminated and the trapping material holding member itself can be regenerated by the thermal desorption process as the regeneration process.

According to fourth aspect of the invention of item 4, the solid trapping material can be held on the trapping material holding member without unevenness. With this, the air-flow resistance can be decreased, and the contact resistance between contaminants and the trapping material can be enhanced.

According to fifth aspect of the invention of item 5, the filtration accuracy of particulate contaminants can be adjusted to high level, and the trapping material can be eliminated and also the trapped particulate contaminants can be incinerated by the regeneration process including the thermal desorption process.

According to sixth aspect of the invention of item 6, by devising the configuration of the gas trapping member, gaseous contaminants can be effectively decomposed, and accordingly the trapping amount of contaminants using the trapping material can be decreased to the extent corresponding to the effective decomposition.

According to seventh aspect of the invention of item 7, gaseous contaminants and particulate contaminants can be trapped, and the trapping performance for predetermined contaminants can be recovered.

According to eighth aspect of the invention of item 8, the trapping performance for predetermined contaminants can be regenerated.

According to ninth aspect of the invention of item 9, the trapping performance for predetermined contaminants can be regenerated by the thermal desorption process.

According to tenth aspect of the invention of item 10, predetermined contaminants can be reliably trapped by the corresponding trapping material.

According to eleventh aspect of the invention of item 11, comparing to a mode without the configuration provided in the invention of item 11, the liquid trapping material can be substantially evenly supplied to the trapping material holding member.

According to twelfth aspect of the invention of item 12, the trapping material can be simply supplied to an existing cleaning filter.

According to thirteenth aspect of the invention of item 13, comparing to a mode without the configuration provided in the invention of item 13, the liquid trapping material can be substantially evenly supplied without waste to the trapping material holding member having the holding region of the trapping material which is formed into a rectangular shape.

According to fourteenth aspect of the invention of item 14, a plurality of kinds of liquid trapping materials can be simply supplied to an existing cleaning filter.

According to fifteenth aspect of the invention of item 15, there can be easily configured an air cleaning apparatus which can trap gaseous contaminants and particulate contaminants, and regenerate or recover the trapping performance for predetermined contaminants.

According to sixteenth aspect of the invention of item 16, gaseous contaminants can be more effectively decomposed, and accordingly the trapping amount of contaminants using the trapping material can be decreased to the extent corresponding to the effective decomposition. Further, heat from the heating means can be effectively used as a heating source for heating, for example.

According to seventeenth aspect of the invention of item 17, there can be easily configured an air cleaning maintenance system which can trap gaseous contaminants and particulate contaminants, and regenerate the trapping performance for predetermined contaminants.

BRIEF DESCRIPTION OF DRAWINGS

FIG. 2 is an explanatory diagram illustrating an air cleaning maintenance system according to a first embodiment of the present invention.

FIG. 10A is an explanatory diagram illustrating an example of a filter cleanliness inspection device used in the first embodiment, FIG. 10B is an explanatory graph showing changes over time of contaminant concentration of a filter to be inspected in an inspection chamber, FIG. 10C is an explanatory diagram illustrating a computational expression for calculating a generation quantity of contaminants by the filter to be inspected, and FIG. 10D is an explanatory diagram illustrating a table example for reference values of generation quantities of predetermined contaminants.

FIG. 19A is an explanatory diagram illustrating a configuration of the separate-type additive supply device used in the sixth embodiment, and FIG. 19B is an explanatory cross-sectional view cut along the B-B line in FIG. 19A.

FIG. 20 is an explanatory diagram illustrating a using method of the separate-type additive supply device used in the sixth embodiment.

DESCRIPTION OF EMBODIMENTS

Overview of Embodiment

Figure 1A:
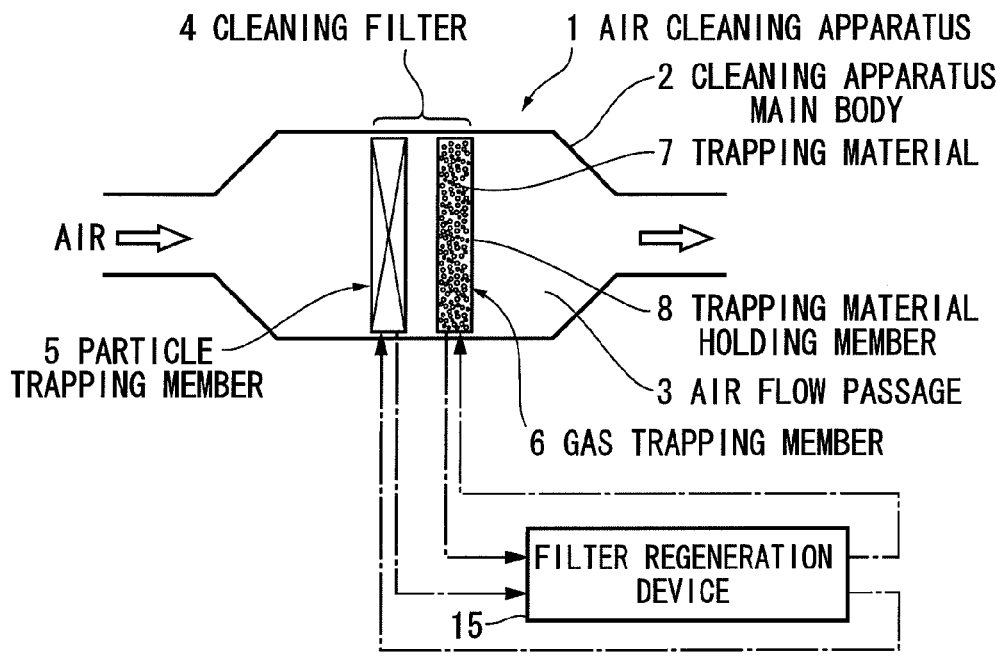
FIG. 1A is an explanatory diagram illustrating an overview of an embodiment of an air cleaning apparatus and an air cleaning maintenance system to which the present invention is applied.

FIG. 1A is an explanatory diagram illustrating an overview of an embodiment of an air cleaning apparatus to which the present invention is applied.

In FIG. 1A, an air cleaning apparatus 1 includes a cleaning apparatus main body 2 in which an air flow passage 3 is formed, and a cleaning filter 4 disposed in the air flow passage 3 of this cleaning apparatus main body 2.

In this embodiment, the cleaning filter 4, which is disposed in the air flow passage 3 of the cleaning apparatus main body 2 of the air cleaning apparatus 1, for cleaning an air passing through the air flow passage 3, includes: a gas trapping member 6 for trapping a gaseous contaminant; and a particle trapping member 5 for trapping a particulate contaminant. At least one of the gas trapping member 6 and the particle trapping member 5 includes: a trapping material 7 for trapping a predetermined contaminant in the air; and a trapping material holding member 8, which is removably mounted on the cleaning apparatus main body 2, for holding the trapping material 7 so as to be opposed to the air flow passage 3 with an air permeability ensured. The trapping material holding member 8 is subjected to, when removed from the cleaning apparatus main body 2, a regeneration process for regenerating trapping performance of the trapping material 7 for the predetermined contaminant under a state in which the trapping material holding member 8 holds the trapping material 7.

In such technical means, the gaseous contaminant refers to a gaseous odor substance or a gaseous chemical substance.

As the particulate contaminant, microbial particles and allergenic particles are mainly considered, but some other substances, such as dust, are also included.

Here, the microbial particles refer to bacteria, fungi, viruses, and the like, and the allergenic particles refer to pollens, mites and their feces, and the like, but a microbial particle may be an allergenic particle as well.

The cleaning filter 4 is supposed to include both the gas trapping member 6 and the particle trapping member 5.

The trapping material 7 is not limited to a solid trapping material, such as active carbon, zeolite, a fabric filter, and a metal filter, but may include various liquid or powder additives.

Here, the additives include chemical adsorbents or impregnation agents for removing odor substances or chemical substances, germicide for sterilizing microorganisms, antimicrobial agents or microbiostatic agents for preventing the development, growth, and proliferation of microorganisms, and also agents for inactivating allergens with respect to the allergenic particles.

The trapping material holding member 8 can be a frame-shaped or container-shaped member for holding the solid trapping material 7 and the like, and can be suitably selected from metallic fibers, non-woven fabrics, or combinations of metallic fibers and non-woven fabrics, which are used for impregnating various additives or holding various additives by impregnation, as long as the trapping material holding member 8 can hold the trapping material 7.

The regeneration process includes a wide variety of processes as long as the process can regenerate the trapping performance of the trapping material 7, and a thermal desorption process, a solvent cleaning, and a supercritical cleaning can be taken as examples thereof.

Next, the following modes can be provided as the cleaning filter 4 to which a thermal desorption process is applied as the regeneration process.

As an example, there is provided a cleaning filter in which the trapping material holding member 8 has a heat resistance, and in which the trapping material 7 having a heat resistance is regenerated by the regeneration process including a thermal desorption process. This is a method of regenerating the trapping material 7 by a thermal desorption process, in which gaseous contaminants trapped in the trapping material 7 such as active carbon are desorbed, or microbial particles or allergenic particles trapped in the trapping material 7 such as metal filter are incinerated.

As another example, there is provided a cleaning filter in which the trapping material holding member 8 has a heat resistance, and in which the trapping material 7 held by the trapping material holding member 8 is eliminated by the regeneration process including a thermal desorption process. This is a method of recovering the trapping material holding member 8 itself to its cleaned state by eliminating the degraded trapping material (mainly additives) by a thermal desorption process.

As a representative mode of the trapping material holding member 8, there is provided a trapping material holding member including: an outer holding frame having an air permeability; and a plurality of baffle plates contained in the outer holding frame, in which the solid trapping material 7 is filled to be distributed with an air permeability ensured. This mode is effective for holding the solid trapping material 7. The baffle plate used here may be formed so as to have a cross section of, for example, trapezoidal waveform, which is provided with a large number of holding hole portions of honeycomb structure, or, alternatively, have a sine wave shape or a rectangular wave shape, which is provided with circular or rectangular holding hole portions.

As another representative mode of the trapping material holding member 8 of the particle trapping member 5, there is provided a trapping material holding member including a plurality of mesh layers each having a different air permeability and made of a material having a heat resistance, the plurality of mesh layers holding an additive as the trapping material 7. This is a particle trapping member which is effective for a regeneration process including a thermal desorption process. The plurality of mesh layers each having a different air permeability may be made of metal or non-woven fabrics.

As a preferred mode of the gas trapping member 6, there is provided a gas trapping member in which the trapping material holding member holds the trapping material 7 for trapping a predetermined gaseous contaminant, and further holds a catalyst particle capable of decomposing the predetermined gaseous contaminant, the catalyst particle being provided upstream of the trapping material 7 in an air flowing direction.

This mode is a method in which gaseous contaminants such as aldehydes are decomposed by catalyst particles (platinum, manganese, and the like). When gaseous contaminants are decomposed, most of the gaseous contaminants are decomposed into water and carbon dioxide which are harmless, but other decomposed products may include some harmful substances. Even if decomposed produces include some harmful substances, the harmful substances are trapped by the trapping material 7 positioned downstream in the air flowing direction so that there is substantially no fear of releasing the harmful substances into an indoor space.

In the air cleaning apparatus including such a gas trapping member 6, the cleaning filter 4 or the cleaning apparatus main body 2 preferably includes heating means capable heating the catalyst particles.

This is a method in which a mode of holding the catalyst particles in the cleaning filter 4 is used, and the heating means is disposed on the cleaning filter 4 or the cleaning apparatus main body 2 in the vicinity of the catalyst particles so as to heat the catalyst particles.

In this mode, for many of the catalyst particles, a decomposition reaction efficiently occurs under temperature higher than room temperature (for example, 200° C. or higher). Then, when the heating means is disposed on the cleaning filter 4 in the vicinity of the catalyst particles, the decomposition efficiency of the catalyst particles is increased due to the heat of this heating means. This mode is preferred in that the generated heat can be used as a heating source for heating in the air cleaning apparatus 1.

Figure 1B:
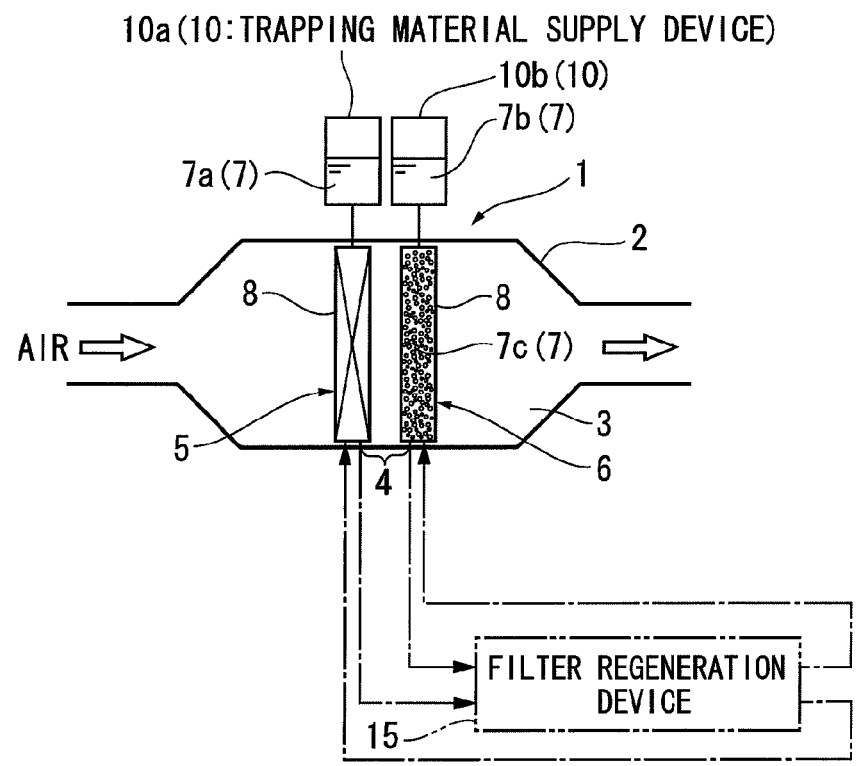
FIG. 1B is an explanatory diagram illustrating an overview of another embodiment of an air cleaning apparatus and an air cleaning maintenance system to which the present invention is applied.

FIG. 1B illustrates another example of an overview of the embodiment of the air cleaning apparatus 1. In FIG. 1B, the air cleaning apparatus 1 includes a cleaning filter 4 which is different from that in FIG. 1A.

The cleaning filter 4, which is disposed in the air flow passage 3 of the cleaning apparatus main body 2 of the air cleaning apparatus 1, for cleaning an air passing through the air flow passage 3, includes: a gas trapping member 6 for trapping a gaseous contaminant; and a particle trapping member 5 for trapping a particulate contaminant. At least one of the gas trapping member 6 and the particle trapping member 5 includes: a trapping material 7 (for example, 7a and 7b) for trapping a predetermined contaminant in the air; a trapping material holding member 8 for holding the trapping material so as to be opposed to the air flow passage with an air permeability ensured; and a trapping material supply device 10 (for example, 10a and 10b) for supplying the trapping material 7 to the trapping material holding member 8 so as to recover trapping performance of the trapping material 7 for the predetermined contaminant.

In this mode, the cleaning filter 4 includes a cleaning filter which is not subjected to the regeneration process.

The supply timing of the trapping material 7 is often periodic, but can be aperiodic without any problems.

In this embodiment, as a representative mode of the trapping material holding member 8, there is provided a trapping material holding member, which is removably mounted on the cleaning apparatus main body 2, and is subjected to, when removed from the cleaning apparatus main body 2, a regeneration process for regenerating the trapping performance of the trapping material 7 for the predetermined contaminant under a state in which the trapping material holding member holds the trapping material 7. This mode is preferred in that the lifetime of the cleaning filter 4 is further extended by the regeneration process.

In particular, as a mode in which the regeneration process including the thermal desorption process is performed, it is only necessary that the trapping material holding member 8 have a heat resistance, and be subjected to the regeneration process including a thermal desorption process.

As a representative mode of the trapping material supply device 10, it is only necessary to selectively supply the trapping material 7 capable of trapping a predetermined contaminant from among the gaseous contaminant and the particulate contaminant.

Here, the word "selectively" not only means individually supplying trapping materials for corresponding contaminants, respectively, but also means supplying mixed trapping materials which are selected corresponding to a plurality of predetermined contaminants.

For example, when the description is made by taking the mode illustrated in FIG. 1B as an example, in order to trap a specific particulate contaminant by the particle trapping member 5, it is only necessary to selectively supply the trapping material 7 (for example, 7a), which can trap the specific particulate contaminant, to the trapping material holding member 8 of the particle trapping member 5. Moreover, in order to trap a specific gaseous contaminant by the gas trapping member 6, it is only necessary to selectively supply the trapping material 7 (for example, 7b), which can trap the specific gaseous contaminant, to the gas trapping member 6. In this case, as a configuration of the gas trapping member 6, the trapping material holding member 8 may hold another trapping material 7 (for example, 7c: active carbon and the like) different from the trapping material 7 (for example, 7b) supplied from the trapping material supply device 10 (for example, 10b).

As a preferred mode of the trapping material supply device 10, there is provided a trapping material supply device including a spray tool capable of spraying a liquid trapping material 7. In this mode, a spray condition of the spray tool for the liquid trapping material 7 is set so that the liquid trapping material 7 is sprayed in an entire holding region of a predetermined trapping material 7 with respect to the trapping material holding member 8.

Here, as the spray tool, other than a spray nozzle, a vaporizer and the like may be suitably selected.

The spray condition for the trapping material 7 only needs to be set so that the trapping material 7 can be sprayed in the entire holding region of the predetermined trapping material 7 with respect to the trapping material holding member 8. For example, the air flow flowing in the air flow passage 3 may be temporarily stopped during spraying, the nozzle-like spray tool may be swung during spraying, or the trapping material 7 may be sprayed toward the air flow flowing in the air flow passage 3 so as to be dispersed with the air flow. These conditions can be suitably selected without any troubles.

Moreover, as the cleaning filter 4, the present invention is not limited to the mode in which the trapping material supply device 10 is equipped all the time, and the trapping material supply device 10 may be configured to be removable when the cleaning filter 4 is used. As a representative mode of the trapping material supply device 10 for such a separate-type cleaning filter 4, there is provided a trapping material supply device, which is removably mounted on the trapping material holding member 8, the trapping material supply device being mounted on the trapping material holding member 8 when supplying the trapping material 7, and being removed from the trapping material holding member 8 when not supplying the trapping material 7.

Here, as a representative mode of the separate-type cleaning filter 4, there is provided a cleaning filter 4 including a trapping material holding member 8 having a holding region of the trapping material 7 which is formed into a rectangular shape. In this mode, the trapping material supply device 10 includes: a spray tool capable of spraying a liquid trapping material 7; and a spray region restricting member, which is disposed on the spray tool or in a spray path of the liquid trapping material 7 from the spray tool, for restricting a spray region shape of the liquid trapping material 7 into a rectangular shape.

In this mode, by restricting the spray region shape of the liquid trapping material 7 into a rectangular shape, the trapping material 7 can be sprayed on the trapping material holding member 8 having the holding region of the holding material 7 which is formed into a rectangular shape, in accordance with the holding region of the trapping material 7.

In view of effectively using the trapping material 7 without waste, the spray region restricting member disposed in the spray path of the trapping material 7 is preferably disposed in close contact with the trapping material holding member 8, and the trapping material 7, which is not held by the trapping material holding member 8, is preferably reused.

As another representative mode of the separate-type cleaning filter 4, there is provided a cleaning filter in which the trapping material supply device 10 includes: a spray tool capable of spraying a plurality of kinds of liquid trapping materials 7; and a trapping material storage container for separately storing the plurality of kinds of liquid trapping materials 7.

In the mode in which the cleaning filter 4 of the air cleaning apparatus 1 is subjected to the regeneration process, the following air cleaning maintenance system can be built.

The air cleaning maintenance system includes: the above-mentioned air cleaning apparatus 1; and a filter regeneration device 15 for regenerating the cleaning filter 4 removed from the air cleaning apparatus 1. The regenerated cleaning filter 4 is reused.

Here, the filter regeneration device 15 widely includes, other than a thermal desorption device, a chemical cleaning device, a supercritical cleaning device, and the like, as long as the device can regenerate the contaminant trapping performance of the cleaning filter 4.

The present invention is described below in more detail based on embodiments illustrated in the accompanying drawings.

First Embodiment

—Overall Configuration of Air Cleaning Maintenance System—

FIG. 2 illustrates an overall configuration of a first embodiment of an air cleaning maintenance system to which the present invention is applied.

In FIG. 2, the air cleaning maintenance system includes an air cleaning apparatus 20 disposed in an indoor space R where a person M lives, and a filter regeneration device 110 for regenerating a cleaning filter 40, which is a component of this air cleaning apparatus 20, temporarily collected by a filter collecting person 100.

—Overview of Air Cleaning Apparatus—

Figure 3:
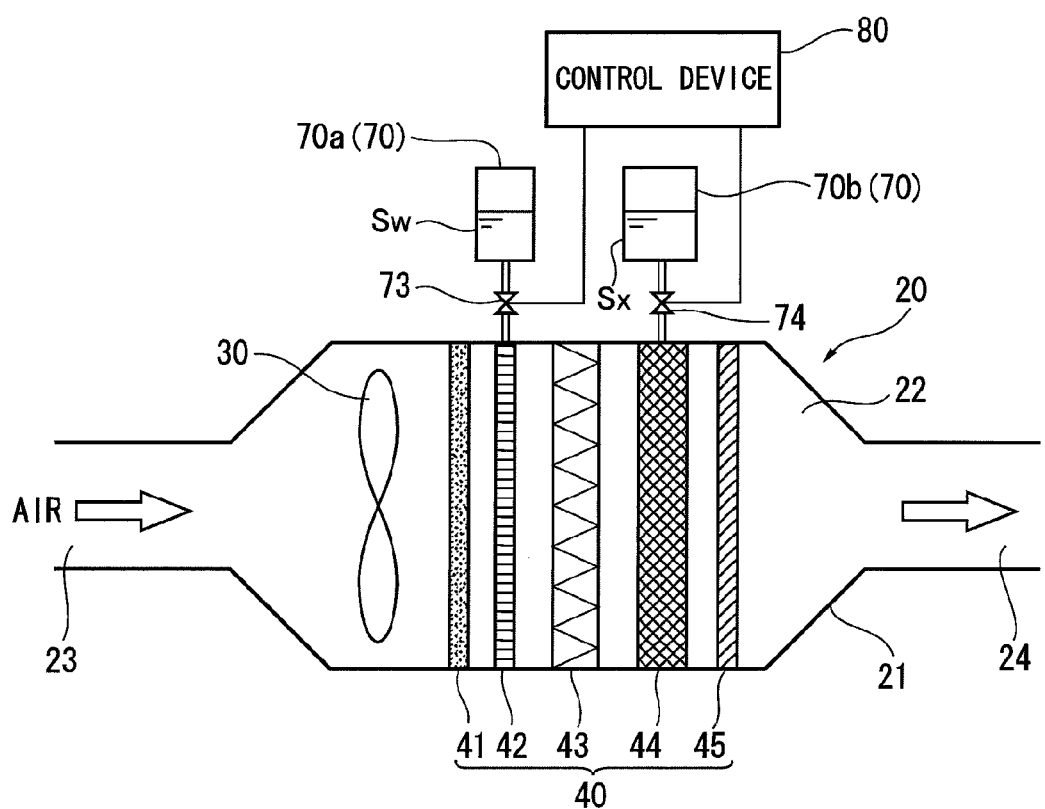
FIG. 3 is an explanatory diagram schematically illustrating an overall configuration of an air cleaning apparatus used in the first embodiment.

In this embodiment, as illustrated in FIG. 3, the air cleaning apparatus 20 includes an air duct 21 as a cleaning apparatus main body in which an air flow passage 22 is defined to be formed. This air flow passage 22 includes on its inlet opening 23 side an intake fan 30 for suctioning air, and includes the cleaning filter 40 on the side downstream of this intake fan 30 in the air flowing direction.

Note that, in this embodiment, the intake fan 30 is disposed in the air duct 21, but the present invention is not limited thereto. A separate ventilation unit may be disposed on the exit side of the air duct 21 so that air is suctioned by this ventilation unit into the air flow passage 22 of the air duct 21.

—Cleaning Filter—

Figure 4:
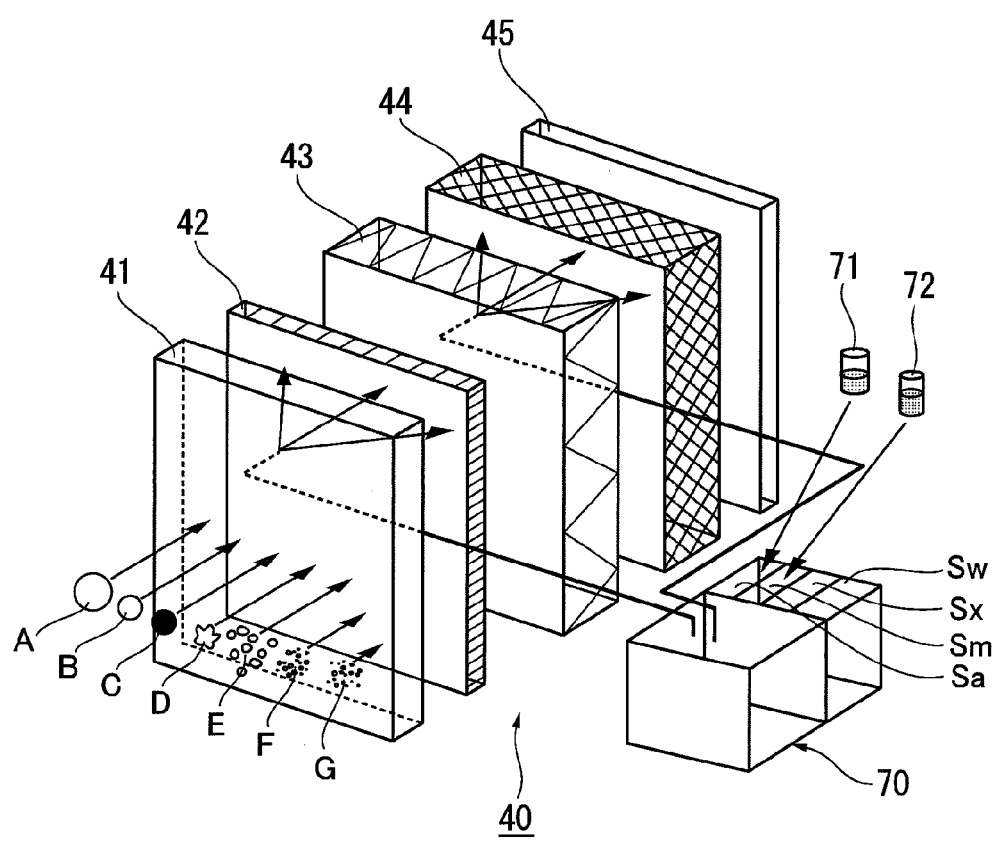
FIG. 4 is an explanatory diagram illustrating details of a cleaning filter used in the first embodiment.

In this embodiment, as illustrated in FIGS. 3 and 4, the cleaning filter 40 is configured by disposing a pre-filter 41, a microorganism removal filter 42, a medium efficiency filter 43, a gas removal filter 44, and a high efficiency particulate air filter (HEPA filter) 45, in this order, from the inlet opening 23 side to an outlet opening 24 side in the air flow passage 22 of the air duct 21.

In this embodiment, the respective filters 41 to 45 are removably mounted in the air duct 21 as the cleaning apparatus main body.

(1) Pre-Filter 41

This is a coarse mesh filter for trapping mainly coarse dust and the like, and is configured by forming metal mesh, metal fibers, carbon fibers, or the like, into a non-woven fabric.

(2) Microorganism Removal Filter 42

This filter is intended to trap mainly microbial particles, such as bacteria, fungi, and virus, but can trap allergenic particles, such as pollens, and mites and their feces, which are similar to microbial particles.

In this embodiment, a thermal desorption process is performed as an example of the regeneration process by the filter regeneration device 110. Therefore, in order to heat the trapped microbial particles and allergenic particles and incinerate the trapped microbial particles and allergenic particles, the configuration requires heat resistance.

Figure 5A:
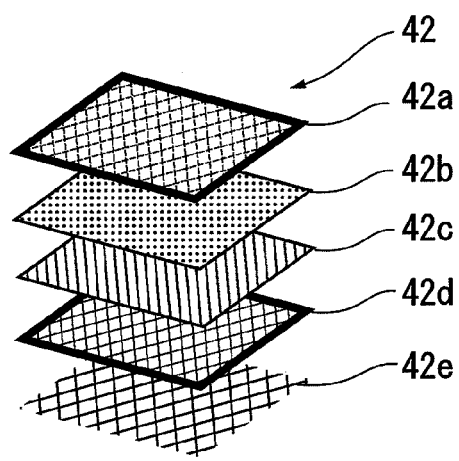
FIG. 5A is an explanatory diagram illustrating a configuration example of a microorganism removal filter which is one of the cleaning filters used in the first embodiment.
Figure 5B:
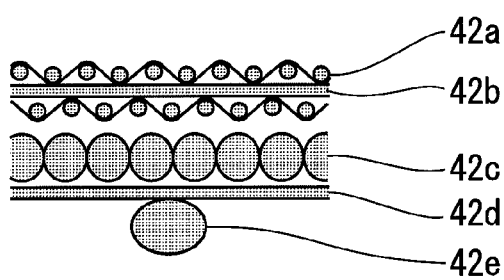
FIG. 5B is an explanatory cross-sectional view of the microorganism removal filter.
Figure 5C:
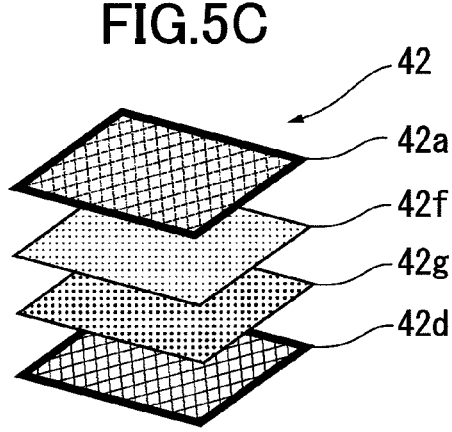
FIG. 5C is an explanatory diagram illustrating another configuration example of the microorganism removal filter.

FIGS. 5A to 5C illustrate configuration examples.

In the mode illustrated in FIGS. 5A and 5B, the microorganism removal filter 42 is configured as a regeneration cartridge which can be regenerated by a thermal desorption process as a regeneration process, and is made of a plurality of mesh layers (42a to 42e) of metal mashes having different air permeabilities, which are laminated in a multistage state. Here, a rigid supporting layer is formed by the coarse mesh layers 42d, 42e. The mesh layer 42a on the surface side is formed as a protective layer, and the fine mesh layers 42b, 42c are formed between the protective layer 42a and the supporting layers 42d, 42e as a filter layer through which microorganisms are hard to pass.

In the mode illustrated in FIG. 5C, the microorganism removal filter 42 is made of a plurality of mesh layers (42a, 42f, 42g, 42d) having different air permeabilities, which are laminated in a multistage state. A rigid supporting layer is formed by the mesh layer 42d made of a coarse metal mesh. A protective layer is formed of the mesh layer 42a of a metal mesh on the surface side, and the fine mesh layers 42f, 42g are formed between the protective layer 42a and the supporting layer 42d by combining a metal mesh and a non-woven fabric as a filter layer through which microorganisms are hard to pass.

Note that, it is understood that the filter having heat resistance may be obtained by forming metal fibers or carbon fibers into a non-woven fabric.

(3) Medium Efficiency Filter 43

This is a mesh filter which is finer than the pre-filter 41, and is intended to trap mainly medium size dust and the like. This filter is configured by forming, for example, metal mesh, metal fibers, or carbon fibers into a non-woven fabric.

(4) Gas Removal Filter 44

This is a filter for removing gaseous contaminants of odor/chemical substances. As illustrated in FIG. 6, for example, this filter has a regeneration cartridge configuration which is available for a thermal desorption process as an example of the regeneration process performed by the filter regeneration device 110 (refer to FIG. 2).

Figure 6A:
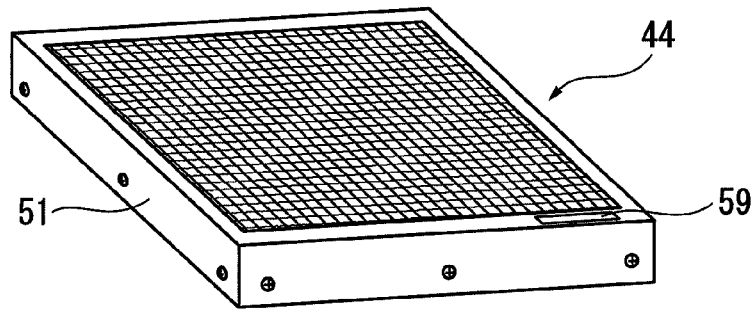
FIG. 6A is an explanatory diagram illustrating an overall configuration of a gas removal filter which is one of the cleaning filters used in the first embodiment.
Figure 6B:
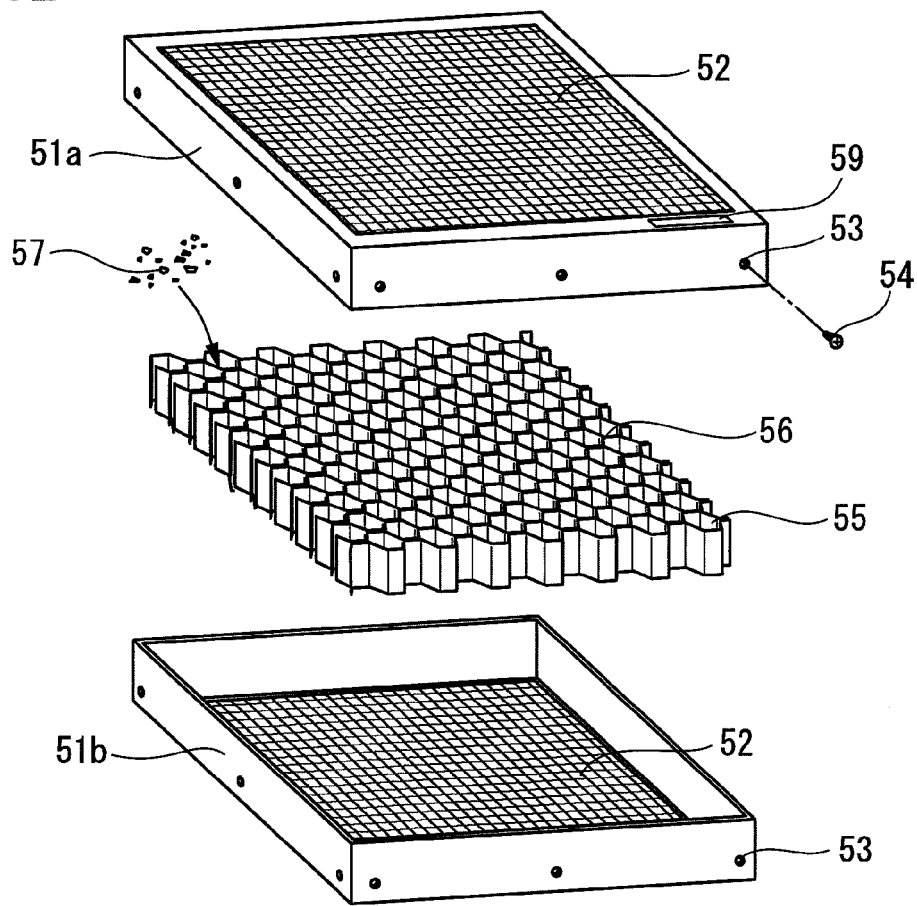
FIG. 6B is an exploded perspective view of the gas removal filter.

In FIGS. 6A and 6B, the gas removal filter 44 includes a box-like outer holding frame 51 made of heat resistant metal, such as stainless steel. This outer holding frame 51 is configured by a pair of dividable holding frame members 51a, 51b having U-shaped cross sections. The top portion of each of the holding frame members 51a, 51b is provided with an opening as an air passage, and a metal mesh 52 is disposed at this opening. The circumference wall of each of the holding frame members 51a, 51b is provided with a suitable number of fixing holes 53, and both the holding frame members 51a, 51b are fixed by fixing tools 54, such as screws.

As illustrated in FIG. 6B, a plurality of baffle plates 55 are arranged in this outer holding frame 51 so that a large number of holding hole portions 56 are formed between the baffle plates 55.

Figure 6C:
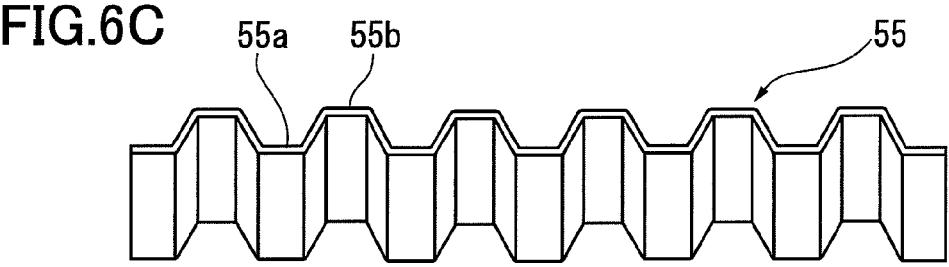
FIG. 6C is an explanatory diagram illustrating a configuration example of a baffle plate of FIG. 6B.

In this embodiment, as illustrated in FIG. 6C, for example, the baffle plates 55 are formed by molding heat resistant metal, for example, a stainless steel plate member, so that trapezoidal cross-sectional portions 55a, 55b are continuously arranged in a waveform. The plurality of baffle plates 55 are arranged so as to ensure the holding hole portions 56 having a honeycomb structure.

The baffle plates 55 have a width size substantially corresponding to the thickness size of the outer holding frame 51, and are arranged so that the above-mentioned holding hole portions 56 penetrate between the metal meshes 52 of the outer holding frame 51.

An adsorbent 57 for adsorbing odor substances and the like, such as active carbon, zeolite, and ceramics, is contained to be held in the holding hole portions 56 defined by the plurality of baffle plates 55.

Such an adsorbent 57 is filled to be distributed in the holding hole portions 56 defined by the baffle plates 55 so that even when the gas removal filter 44 is arranged in the vertical direction, the adsorbent 57 is not unevenly disposed in the outer holding frame 51.

Moreover, in this embodiment, a portion of the opening edge portion of the outer holding frame 51 of the gas removal filter 44 is provided with an owner indication portion 59 on which an owner number (a number indicating an owner of the gas removal filter 44) is impressed.

(5) HEPA Filter 45

This is a mesh filter which is further finer than the medium efficiency filter 43, and is intended to trap fine powders of the active carbon used in the gas removal filter 44, or the like. This filter is configured by forming, for example, metal mesh, metal fibers, or carbon fibers, into a non-woven fabric.

—Additive Supply Device—

In this embodiment, the cleaning filter 40 is provided with an additive supply device 70 which can supply additives corresponding to, for example, microbial particles and gaseous contaminants, such as volatile organic compounds (VOCs), which are intended to be removed by the microorganism removal filter 42 and the gas removal filter 44.

As illustrated in FIGS. 3 and 4, this additive supply device 70 includes additives corresponding to the removal of odor substances and chemical substances (for example, an additive Sa corresponding to ammonia, an additive Sm corresponding to methyl mercaptan, or a mixed additive Sx corresponding to a plurality of odor/chemical substances including the above-mentioned substances), and an additive Sw corresponding to the removal of microorganisms (for example, germicides corresponding to the sterilization of microorganisms, or antimicrobial agents corresponding to the prevention of proliferation of microorganisms).

For example, these additives are individually contained in corresponding additive bottles 71, 72, and are suctioned in a given quantity from the respective additive bottles 71, 72 by a pump (not shown) so as to be periodically sprayed.

In FIG. 3, an additive supply device 70a is a component for supplying, for example, the additive Sw corresponding to the removal of microorganisms, and an additive supply device 70b is a component for supplying, for example, the additive Sx.

A control device 80 is configured to control opening and closing of respective on-off valves 73, 74 so that the additive Sw in the additive supply device 70a is periodically supplied in a given quantity to the microorganism removal filter 42 in accordance with opening and closing of the on-off valve 73, and the additive Sx in the additive supply device 70b is periodically supplied in a given quantity to the gas removal filter 44 in accordance with opening and closing of the on-off valve 74. It is understood that the opening and closing control of the on-off valves 73, 74 may be performed by simply opening and closing the on-off valves 73, 74, or by adjusting the opening degrees of the on-off valves 73, 74.

—Function of Cleaning Filter—

As illustrated in FIG. 4, for example, assuming that there exist dust A, pollen B, fungi C, bacteria D, virus E, chemical substances F, and odor substances G, as contaminants in the air, the dust A is trapped by mainly the pre-filter 41, the medium efficiency filter 43, and the HEPA filter 45, the fungi C, the bacteria D, and the virus E, are trapped by mainly the microorganism removal filter 42, and the chemical substances F and the odor substances G are trapped by mainly the gas removal filter 44. The pollen B is trapped by the microorganism removal filter 42 and the medium efficiency filter 43.

At this time, in this embodiment, the corresponding additives S are periodically sprayed on the microorganism removal filter 42 and the gas removal filter 44, and hence the removal performances for odor substances, chemical substances, and microorganisms are periodically recovered.

In this embodiment, the additives S are sprayed on the microorganism removal filter 42 and the gas removal filter 44, but the present invention is not limited thereto. The additives S may be sprayed on the dust removal filters, such as the medium efficiency filter 43, as needed.

In this embodiment, the filters can be configured depending on the contamination state of the space where the air cleaning apparatus 20 is installed. That is, conventional gas or dust removal filters are applied with impregnation agents which are effective for general contaminants, on the assumption of a general contamination state.

On the other hand, in this embodiment, additives can be selected depending on the types and physical/chemical properties of contaminants in the air cleaning apparatus installation room.

For example, when the main contaminants in the space are fungi (mold) and bacteria, germicide, antimicrobial agents, and microbiostatic agents, which are effective for the species, only need to be sprayed on the microorganism removal filter 42 and the dust removal filters, such as the medium efficiency filter 43. When the main contaminants in the space are ammonia, the additive Sa corresponding to ammonia only needs to be sprayed. Moreover, when a plurality of contaminants need to be removed from the space, such as formaldehyde, methyl mercaptan, and hydrogen sulfide, the additives Sf, Sm, Ss corresponding to the respective contaminants only need to be supplied from the respective additive bottles, or supplied in a mixed state.

Note that, when many allergenic particles, such as pollens, exist in the space, agents for inactivating the allergenic particles only need to be supplied as additives to, for example, the microorganism removal filter 42. When many odor substances, such as tobacco smell, roast smell, and pet smell, exist in the space, additives corresponding to the odor substances only need to be supplied.

In this embodiment, the additives such as germicide, antimicrobial agents, and microbiostatic agents are sprayed on and impregnated into the microorganism removal filter 42. Therefore, the microorganism removal filter 42 is preferred not to be deteriorated by the additives, and the additives are preferably hard to be volatilized by the air flow of the intake fan 30. Even if the additives are volatilized and conveyed, because the gas removal filter 44 is disposed on the downstream side of the air flow passage 22, the additives are effectively prevented from unnecessarily diffusing into the room.

—Filter Regeneration Device—

In this embodiment, additives are periodically supplied to the microorganism removal filter 42 and the gas removal filter 44, but, when these filters have been used over a long period of time, the total amount of additives may become excessive so as to cause negative effects on the regeneration of performance.

Therefore, in this embodiment, as illustrated in FIG. 2, the filter collecting person 100 temporarily collects the corresponding filters, and these filters are processed by the filter regeneration device 110 so as to be regenerated.

Here, as the filter regeneration device 110, there are provided a thermal desorption device 111 and a chemical cleaning device 112, for example.

(1) Thermal Desorption Device 111

This device is configured to apply a thermal desorption process to the microorganism removal filter 42 and the gas removal filter 44 because these filters are configured as regeneration cartridges.

Figure 7:
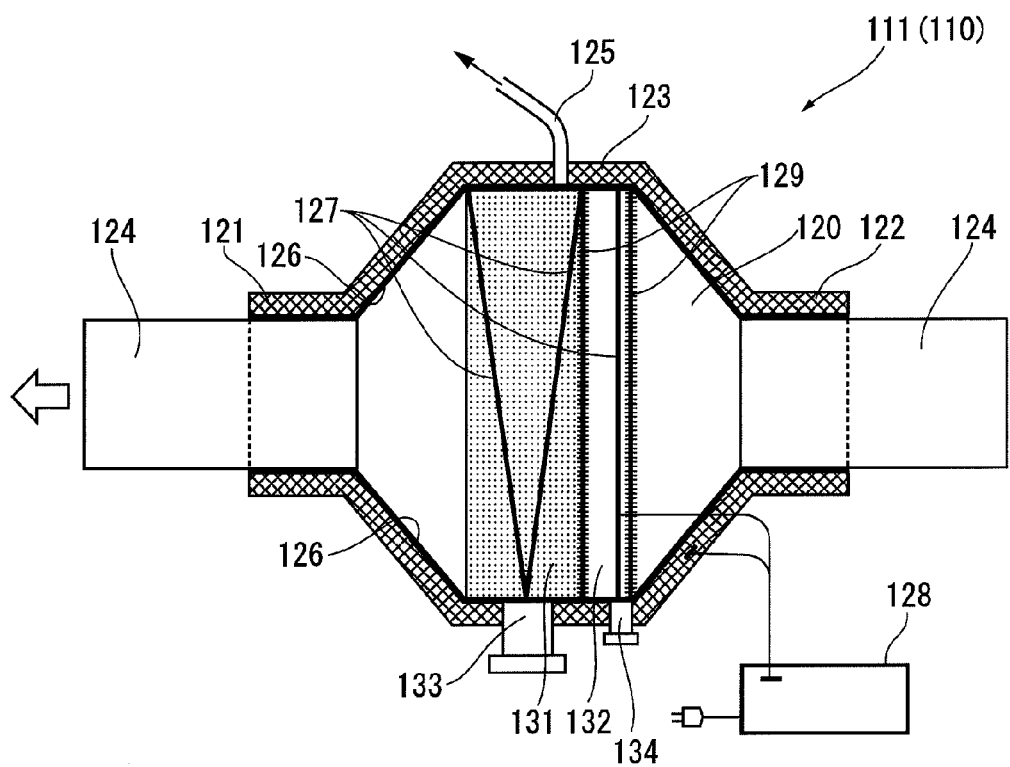
FIG. 7 is an explanatory diagram illustrating details of a thermal desorption device which is an example of a filter regeneration device used in the first embodiment.
Figure 8:
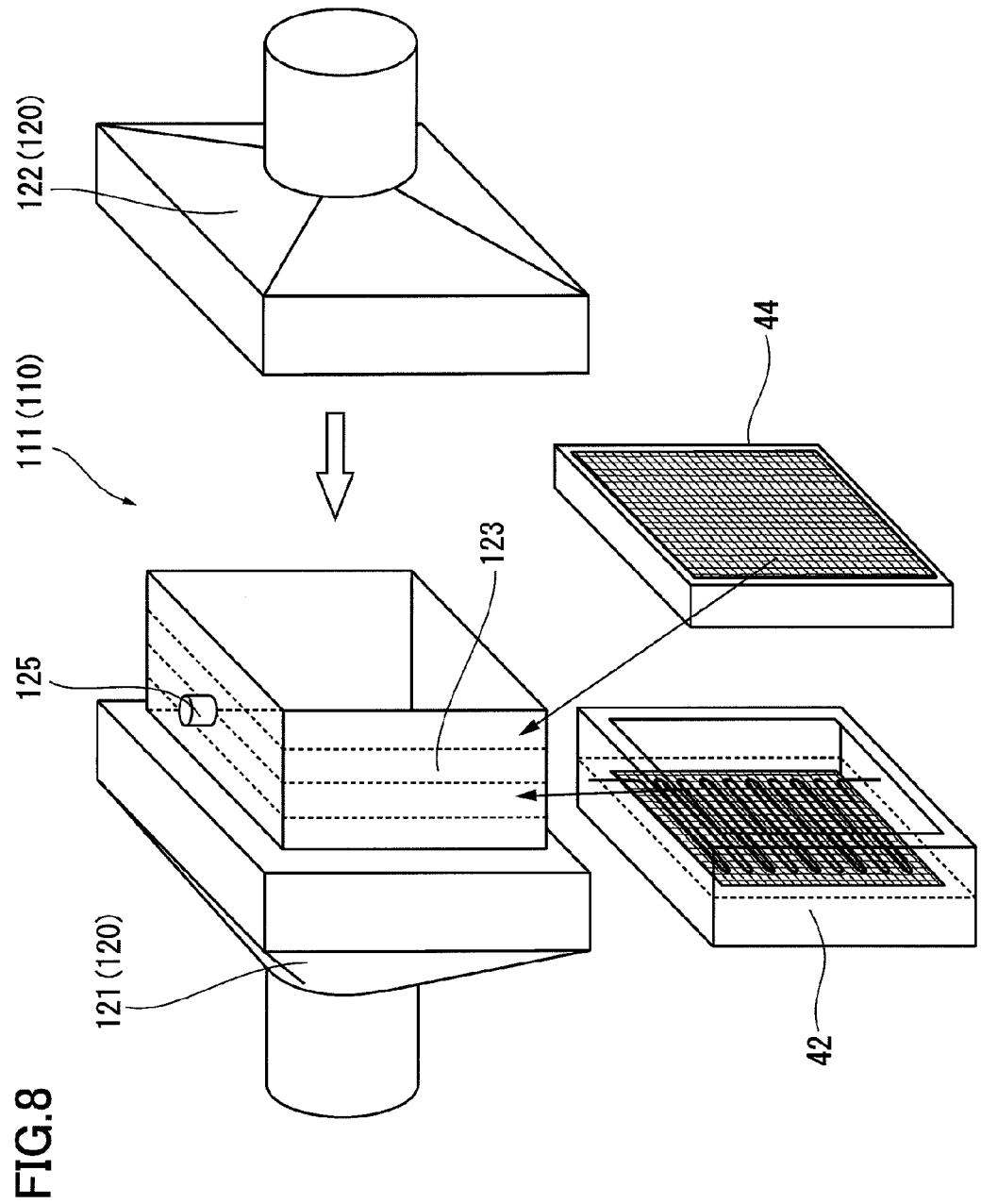
FIG. 8 is an explanatory diagram illustrating a relationship between the thermal desorption device illustrated in FIG. 7 and respective filters to be processed by the thermal desorption device.

In this embodiment, as illustrated in FIGS. 7 and 8, the thermal desorption device 111 includes a heat-resistant casing 120 formed of a plurality of divided heat-resistant chambers 121, 122. A filter containing portion 123 (specifically, a portion 131 corresponding to the microorganism removal filter 42 and a portion 132 corresponding to the gas removal filter 44) is disposed at one heat-resistant chamber 121 of this heat-resistant casing 120. This filter containing portion 123 is provided with an exhaust port 125. The portion corresponding to the filter containing portion 123 is provided with heaters 126, 127, and the above-mentioned heaters 126, 127 are heated by a temperature controller 128 to a predetermined temperature (for example, about 200° C. to 500° C.).

Reference symbol 124 represents a heat-resistant connection duct; 129, a filter holding wall of the filter containing portion 123; and 133, 134, maintenance ports for visually inspecting the inside of the filter containing portions 123 when the respective microorganism removal filter 42 and gas removal filter 44 are contained therein.

In this embodiment, the contaminants collected in the microorganism removal filter 42 are incinerated, and the added additives are desorbed to be removed. As a result, the microorganism removal filter 42 is regenerated into a cleaned state.

Moreover, the contaminants trapped by the adsorbent 57 of the gas removal filter 44 and the additives are desorbed to be removed. As a result, the adsorption performance of the adsorbent 57 is regenerated.

In particular, in this embodiment, the heating temperatures of the heaters 126, 127 are set to about 300° C. to 350° C. so that the microorganism removal filter 42 and the gas removal filter 44 are effectively regenerated.

(2) Chemical Cleaning Device 112

In this embodiment, the chemical cleaning device 112 can clean dirty dust removal filters, such as the medium efficiency filter 43, by predetermined chemicals.

—Contaminant Analysis Device 160—

In this embodiment, when performing the regeneration process by the thermal desorption device 111 or the chemical cleaning device 112, the contaminants removed from the respective filters 42, 44 can be analyzed so that the state of contaminants in the space where the collected cleaning filter 40 is installed can be analyzed.

In this case, as the contaminant analysis device 160 (refer to FIG. 2), there is employed a gas chromatograph, a gas chromatograph mass spectrometer, a high performance liquid chromatograph, an ion chromatograph, or the like, and a gas collected by a collecting member is to be analyzed.

Figure 9A:
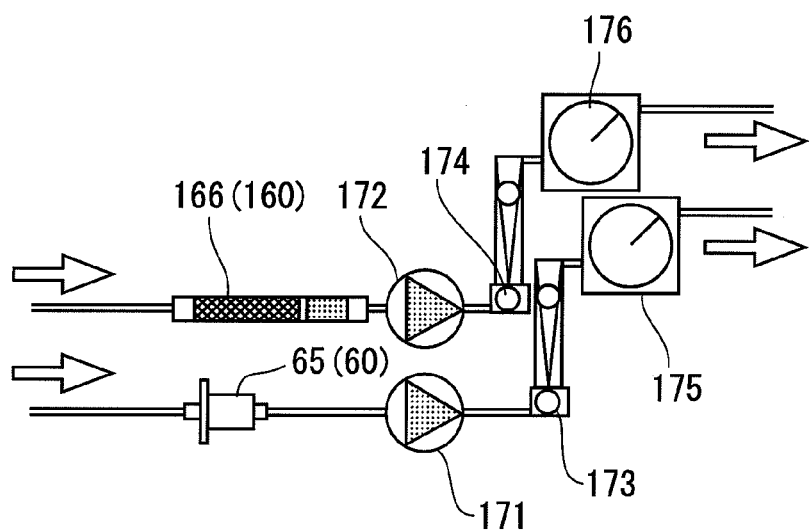
FIGS. 9A and 9B are explanatory diagrams respectively illustrating different examples of a contaminant analysis device used in the first embodiment.

Further, as the collecting member, for example, as illustrated in FIG. 9A, there are used an HCHO collecting tube 165 for collecting HCHO from among the VOCs, and a collecting tube 166 for collecting VOCs other than HCHO. In this embodiment, as the HCHO collecting tube 165, there is used an HCHO collecting tube that employs 2,4-dinitrophenylhydrazine (DNPH) as a collecting agent, and further, as the collecting tube 166 for collecting other VOCs, a carbon-based collecting agent or Tenax TA is used.

Further, the contaminant analysis device 160 sends the VOCs collected by the collecting tubes 165, 166 to flow meters 173, 174 and gas meters 175, 176 via pumps 171, 172, respectively, to thereby perform a qualitative analysis and a quantitative analysis on the VOCs.

Figure 9B:
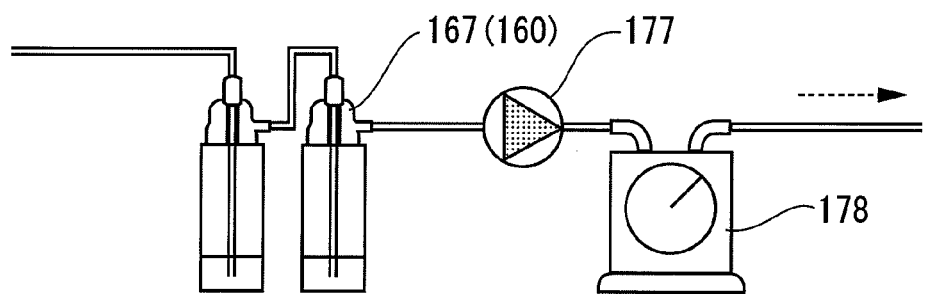

Note that, as another mode of the collecting member, for example, as illustrated in FIG. 9B, a collecting tube 167 formed of an impinger may be used, for example, so that the collected VOCs are sent to a gas meter 178 via a pump 177 to perform a qualitative analysis.

—Filter Cleanliness Inspection Device—

In this embodiment, the cleaning filter 40 regenerated by the filter regeneration device 110 can be inspected for the cleanliness of the cleaning filter 40 by a filter cleanliness inspection device 200 (refer to FIG. 2).

In FIG. 10A, the filter cleanliness inspection device 200 includes an inspection chamber 201, a holding mechanism (not shown), a fan unit 210, and a detector 220. The inspection chamber 201 is configured so that cleaned air is supplied via a supply port 202 and exhausted via an exhaust port 203, and also diffused by a diffusing fan 205. The holding mechanism (not shown) is disposed in this inspection chamber 201 so as to releasably hold the gas removal filter 44 (42) as a component of the cleaning filter 40 to be inspected. The fan unit 210 is configured to cause the air in the inspection chamber 201 to pass through the filter 44 (42) held by the holding mechanism. The detector 220 is disposed downstream of the air flow generated by the fan unit 210 and passing through the filter 44 (42), and is configured to detect contaminants which affect the cleanliness of the filter 44 (42).

In this embodiment, the cleanliness of the filter 44 (42) can be determined based on the output from the detector 220 in a short time.

That is, as shown in FIG. 10B, the concentration of contaminants in the inspection chamber 201 changes with the lapse of time.

At this time, the generation quantity of contaminants can be obtained based on the computational expression illustrated in FIG. 10C.

The parameters in FIG. 10C are as follows.

$$m = Q + \alpha R$$

α: adsorption rate of the subject contaminant to the inspection chamber (1/h)

R: chamber air volume ($m^3$)

Q: chamber ventilation quantity ($m^3/h$)

C: concentration of the subject contaminant in the chamber at a given arbitrary time t ($\mu g/m^3$)

t: time $C_0$: concentration of the subject contaminant in the chamber supply air $C_1$: concentration of the subject contaminant in the chamber when starting the experiment M: contaminant generation quantity ($\mu g/h$)

Based on the relationship between the value calculated as described above and the generation quantity reference values shown in FIG. 10D, the level of the contaminant generation quantity M of the filter to be inspected can be determined.

As a result, the contaminant generation quantity M equal to or smaller than the permissible value is determined to be "OK", and the contaminant generation quantity M exceeding the permissible value is determined to be "NG".

In the case of "OK", the cleanliness of the subject filter is determined to be sufficient, and the filter is delivered to the user with no process subjected thereto. On the other hand, in the case of "NG", the cleanliness of the subject filter is determined to be insufficient, and it is only necessary that the regeneration process be performed again by the filter regeneration device 110 and then the filter cleanliness inspection be performed again.

Modified Mode

FIG. 11 illustrate a modified mode of the gas removal filter 44 used in the first embodiment.

Figure 11A:
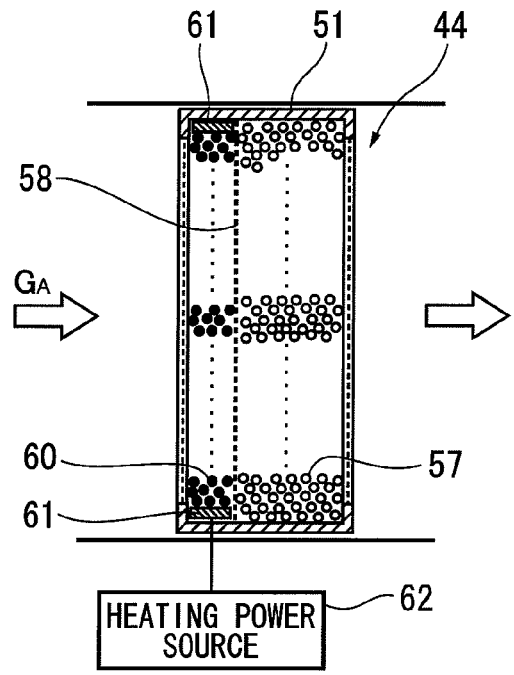
FIG. 11A is an explanatory diagram illustrating a modified mode of the gas removal filter used in the first embodiment.

In FIG. 11A, the gas removal filter 44 holds the adsorbent 57, such as active carbon, in the outer holding frame 51, and also holds catalyst particles 60, which can decompose gaseous contaminants, on the upstream side of the adsorbent 57 in the air flowing direction. Reference symbol 58 represents a partition plate which partitions the space in the outer holding frame 51 with the air permeability ensured.

Figure 11B:
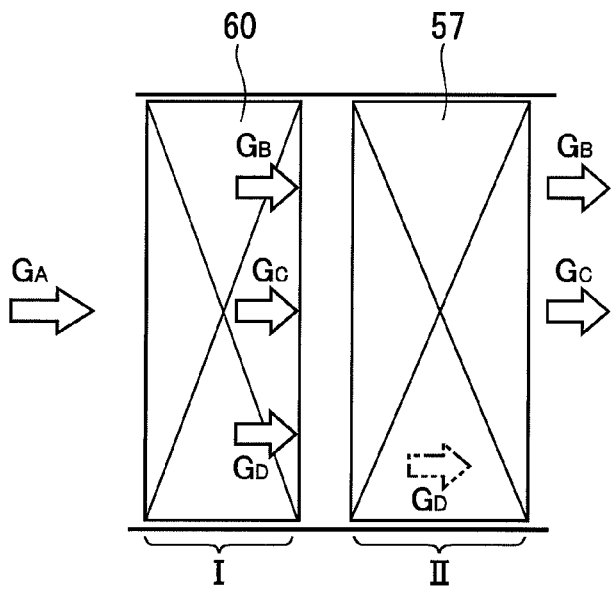
FIG. 11B is an explanatory diagram illustrating a function of the gas removal filter according to the modified mode.

In this mode, as illustrated in FIG. 11B, the catalyst particles 60 (platinum, manganese, or the like) in Region I decompose gaseous contaminants $G_A$, such as aldehydes, so that most of the gaseous contaminants $G_A$ react into harmless water $G_B$ and carbon dioxide $G_C$, but decomposed products $G_D$ other than the above may include some harmful substances. Even if some harmful substances are included in the decomposed products $G_D$, such harmful substances are trapped by the adsorbent 57 in Region II positioned on the downstream side in the air flowing direction so that there is substantially no fear of releasing the harmful substances into an indoor space.

In this embodiment, a heater 61 is disposed in the outer holding frame 51 of the gas removal filter 44 (refer to FIG. 11A), and this heater 61 is configured to be heated by a heating power source 62 to, for example, 200° C. or higher.

In this mode, many of the catalyst particles 60 cause a decomposition reaction efficiently under temperature higher than normal temperature (for example, 200° C. or higher). Accordingly, the decomposition efficiency of the catalyst particles 60 is increased by the heat from the heater 61. At this time, the generated heat is used as a heating source when heating as the air cleaning apparatus 20.

Second Embodiment

Figure 12:
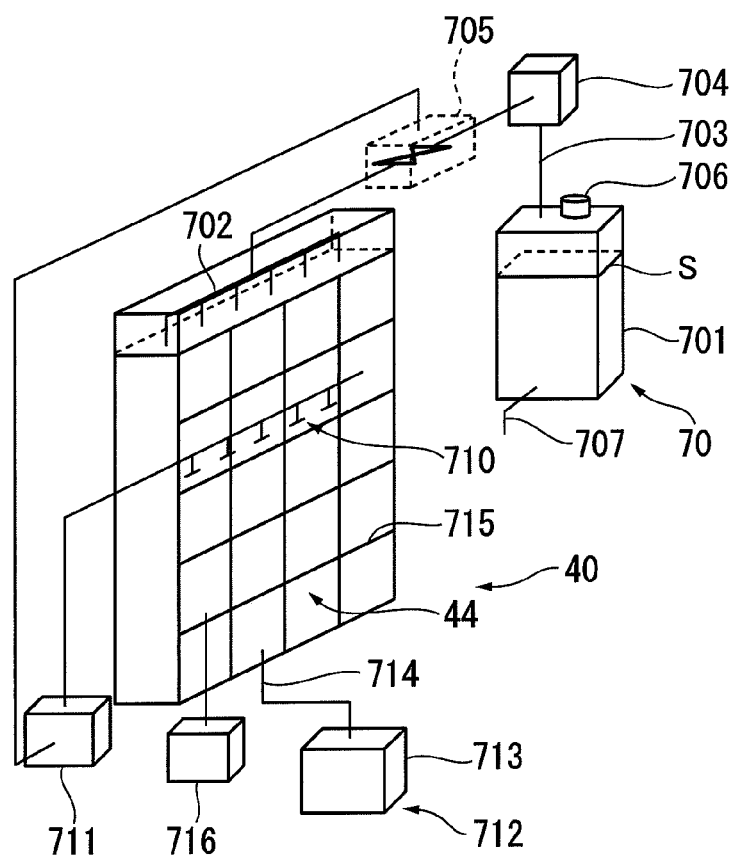
FIG. 12 is an explanatory diagram illustrating a main part of an air cleaning apparatus according to a second embodiment of the present invention.

FIG. 12 illustrates a main part of a cleaning filter 40 of an air cleaning apparatus according to a second embodiment the present invention.

In this embodiment, the cleaning filter 40 includes a filter element substantially similar to that of the first embodiment, and is configured so that, for example, an additive supply device 70 is disposed adjacent to the gas removal filter 44.

In this embodiment, the additive supply device 70 includes an additive supply tank 701 which stores an additive S for removing odor substances and chemical substances. At the upper portion of the gas removal filter 44, a uniform distribution nozzle 702 is disposed by substantially evenly arranging a plurality of nozzle portions along the length direction of the upper edge of the gas removal filter 44. The above-mentioned additive supply tank 701 and uniform distribution nozzle 702 are connected to communicate to each other via a supply tube 703. In the middle of this supply tube 703, a pump 704 and a flow rate adjusting valve 705 are interposed. Note that, as the additive S in this embodiment, when the subject contaminant is formaldehyde, for example, a formaldehyde catching agent is used, and when the subject contaminant is a mixed gas of formaldehyde and VOC, a graft polymerization agent is used. In FIG. 12, reference symbol 706 represents a supply port of the additive supply tank 701, and reference symbol 707 represents a drain tube thereof.

Moreover, in this embodiment, there are provided in the gas removal filter 44 a suitable number of concentration sensors 710 for detecting the concentration of the impregnated additive S. The information from the concentration sensors 710 is input into a flow rate control device 711. This flow rate control device 711 controls the injection quantity of a chemical solution (additive) by adjusting the opening degree of the flow rate adjusting valve 705. The flow rate control device 711 is operated based on the sensor outputs from the above-mentioned concentration sensors 710 as feedback signals, and has a concentration adjusting mode for controlling the injection quantity of the chemical solution so as to maintain, at a fixed value, the chemical solution concentration at the filter substrate of the gas removal filter 44.

Moreover, in this embodiment, in addition to the above-mentioned mode, the flow rate control device 711 has a periodical supply mode for supplying a chemical solution every fixed period using a timer.

In this embodiment, the cleaning filter 40 further includes a drain device 712 capable of draining liquid waste of the additive S. This drain device 712 is configured by disposing a drain tank 713 below the gas removal filter 44, and connecting the drain tank 713 to the gas removal filter 44 via a drain tube 714 to communicate to each other, to thereby drain excess additives S to the drain tank 713.

In this embodiment, a filter heating device 715 is disposed on the ventilation surface of the gas removal filter 44. This filter heating device 715 is formed by, for example, heating wires arranged in a crossing state in the substantially entire ventilation surface of the gas removal filter 44. For example, the filter heating device 715 is periodically heated based on a control signal from a heating control device 716 so that additive reaction products accumulated in the filter substrate of the gas removal filter 44 are periodically removed. In this case, in order not to contaminate the room by the removed additive reaction products, for example, a physical adsorbent, such as active carbon, may be disposed, or the removed additive reaction products may be released via an exhaust duct (not shown) to the outside. Note that, instead of the filter heating device 715, a method of chemically processing predetermined reaction products may be suitably adopted.

Therefore, according to the air cleaning apparatus of this embodiment, contaminated air to be cleaned is taken in the air flow passage by an intake fan (not shown). At this time, large particles among the particles, such as dust, in the air to be cleaned are removed by the pre-filter (not shown). Next, fine particles, which have passed through the pre-filter, are removed by the microorganism removal filter and the medium efficiency filter. Further, gaseous chemical substances, such as formaldehyde, are removed by the gas removal filter 44. Finally, products from the gas removal filter 44 or the like are removed by the HEPA filter.

Particularly, according to the cleaning filter 40 of this embodiment, the liquid additive (liquid agent) S is replenished and supplied to the filter substrate of the gas removal filter 44 as needed, and is substantially uniformly distributed by the uniform distribution nozzle 702. Accordingly, the filter substrate of the gas removal filter 44 is maintained in a state in which the impregnation degree of the liquid agent S is substantially uniform over a long period of time. Thus, the gas removal performance of the gas removal filter 44 is stably maintained over a long period of time. At this time, the liquid agent S does not need to be constantly supplied to the gas removal filter 44, and hence there is no fear that the liquid agent S is consumed in an unnecessary manner.

Note that, in this embodiment, the concentration sensors 710 are disposed in the middle of the gas removal filter 44 so as to detect the concentration of the liquid additive (liquid agent) S impregnated in the filter substrate of the gas removal filter 44. However, an impregnation sensor may be disposed in the vicinity of the lower end portion of the filter substrate of the gas removal filter 44. With this, the impregnation state of the liquid agent S in the filter substrate is detected based on a signal from the impregnation sensor, and the flow rate adjusting valve 705 is controlled in accordance with the signal from the impregnation sensor. Moreover, in this embodiment, the gas removal filter 44 includes a single row of the filter substrate, but the present invention is not limited thereto. For example, a plurality of rows of filter substrates may be used so as to enlarge the area of the filter substrates with which the ventilation comes into contact. Alternatively, the filter substrate may be provided with a bellows-like folded portion so as to enlarge the substantial area of the filter substrate with which the ventilation comes into contact.

Third Embodiment

Figure 13:
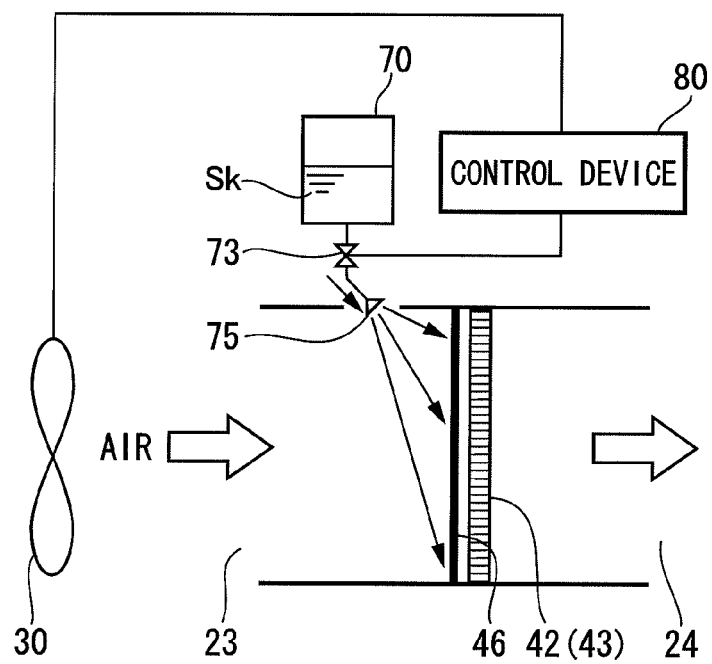
FIG. 13 is an explanatory diagram illustrating a main part of an air cleaning apparatus according to a third embodiment of the present invention.

FIG. 13 illustrates a main part of a clean filter 40 of an air cleaning apparatus according to a third embodiment the present invention.

In FIG. 13, the cleaning filter 40 includes, for example, a non-woven fabric 46 is disposed upstream of, for example, the microorganism removal filter 42 (or the medium efficiency filter 43) in the air flowing direction. The additive supply device 70, which can supply, for example, the additive (liquid agent) Sk including an antimicrobial agent, may periodically spray a fixed amount of the additive Sk to the above-mentioned non-woven fabric 46 via a spray nozzle 75.

Note that, the components similar to those of the first embodiment are represented by the same reference symbols as those of the first embodiment, and their details are not described here.

According to this embodiment, when an antimicrobial agent corresponding to a virus, such as an influenza virus, is supplied as the additive Sk, infection by the virus can be effectively prevented.

In this embodiment, the non-woven fabric 46 is separately disposed, but the additive can be directly sprayed on the microorganism removal filter 42 (or the medium efficiency filter 43).

In this embodiment, the additive (liquid agent) S needs to be sprayed uniformly in the entire filter surface of the cleaning filter 40. At this time, in the mode in which the spray angle of the additive Sk is fixedly set at the spray nozzle 75, the spray range of the additive Sk may be restricted by the air flow generated by the intake fan 30 of the air cleaning apparatus.

Therefore, this embodiment adopts a method in which the opening and closing operations of the on-off valve 73 and the operation of the intake fan 30 are performed in association by the control device 80, and for example, when the additive Sk is being sprayed by the spray nozzle 75, the intake fan 30 is temporarily stopped.

Figure 14A:
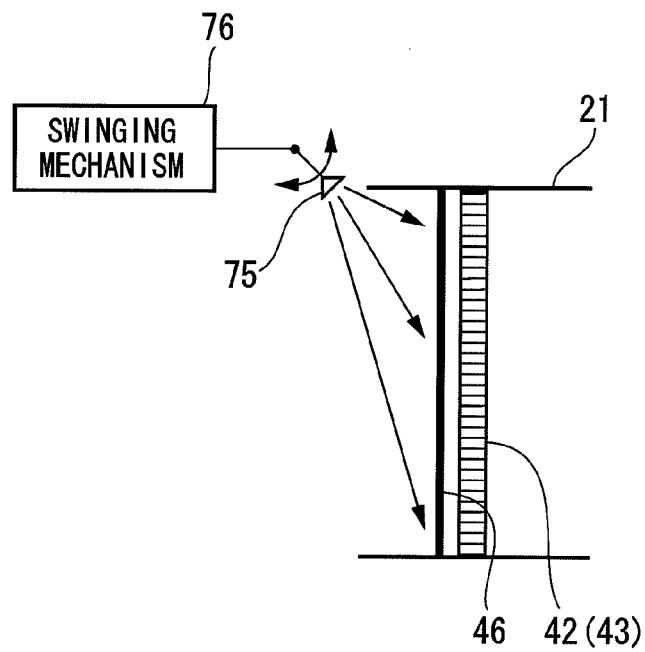
FIGS. 14A and 14B are explanatory diagrams illustrating a modified mode of an additive supply device used in the third embodiment.
Figure 14B:
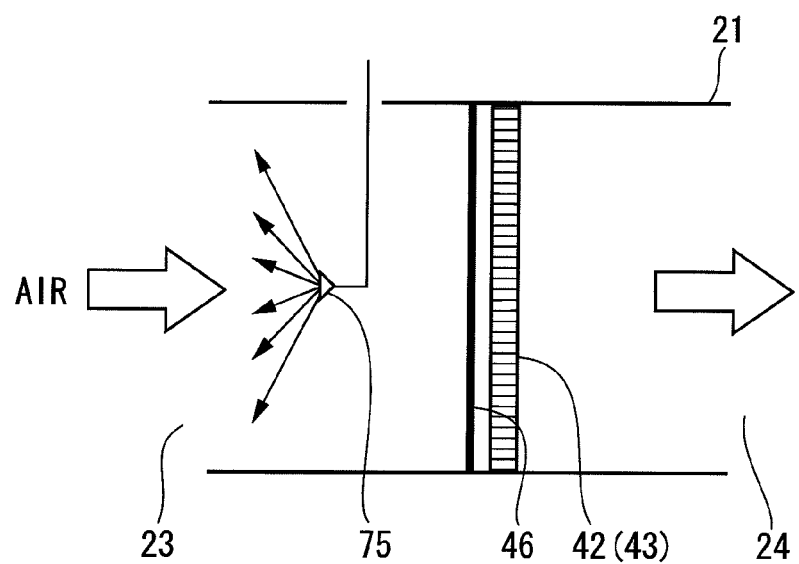

The spray operation of the additive Sk by this spray nozzle 75 is not limited to the above-mentioned method, and can be suitably selected from among the following methods. For example, as illustrated in FIG. 14A, while swinging the spray nozzle 75 by a swinging mechanism 76, the additive Sk is sprayed in a wide range. Alternatively, as illustrated in FIG. 14B, the liquid additive Sk is sprayed from the spray nozzle 75 against the air flow generated by the intake fan 30 so that the additive Sk is dispersed by a collision between the air flow and the sprayed additive Sk.

Moreover, in this embodiment, the additive supply device 70 adopts the spray nozzle 75 as a spray tool, but the present invention is not limited thereto as long as the spray tool is capable of spraying the liquid additive Sk. There can be adopted, for example, a mode using an ultrasonic atomization method, a mode using a thermal vaporization method, or a mode using a rotary atomization method.

Figure 15B:
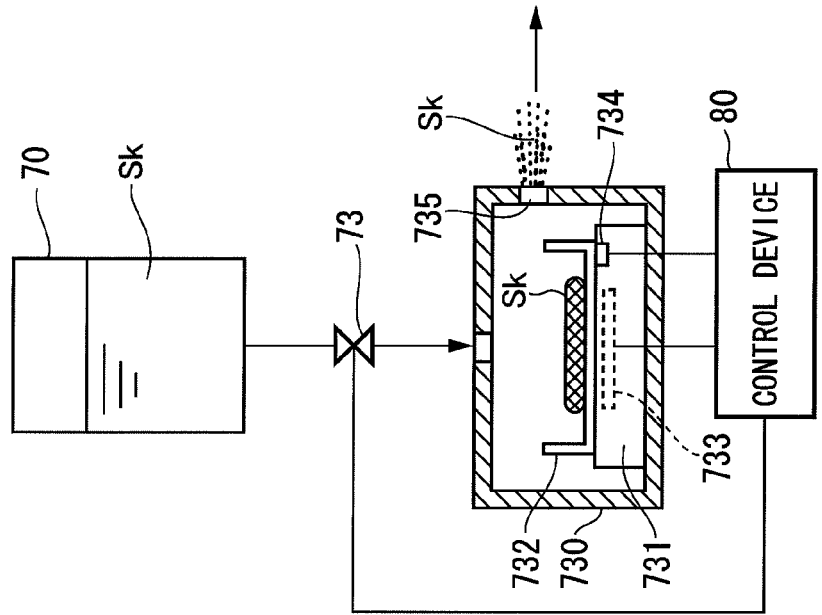
FIGS. 15A and 15B are explanatory diagrams illustrating spray tools other than a nozzle of the additive supply device used in the third embodiment.
Figure 15A:
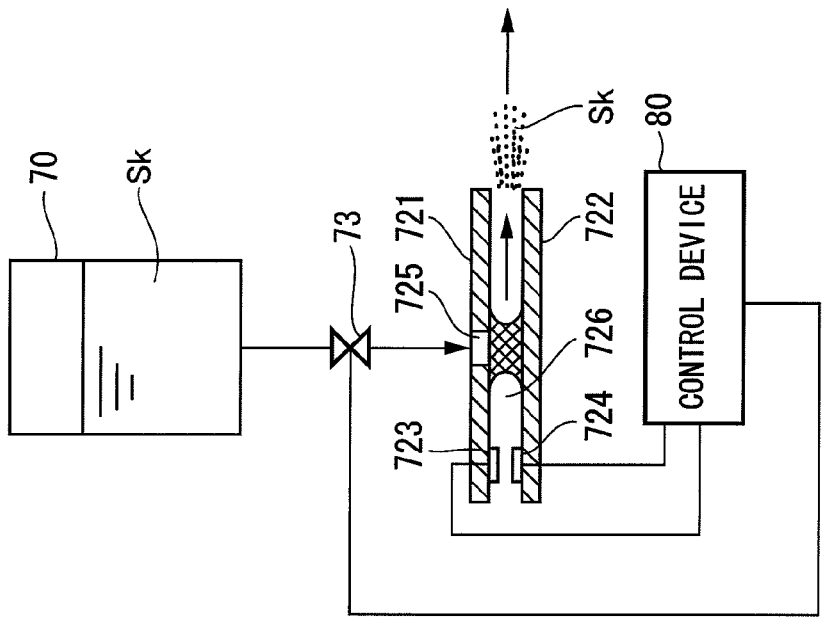

For example, as the mode using an ultrasonic atomization method, as illustrated in FIG. 15A, the following mode can be provided. A pair of surface acoustic wave (SAW) elements 721, 722 is disposed so that the surfaces thereof, on which interdigital transducers (IDT) 723, 724 of the respective SAW elements 721, 722 are disposed, are opposed to each other. For example, the liquid additive Sk is supplied into a flow passage 726 between the SAW elements 721, 722 via a through hole 725 of one SAW element 721, and ultrasonic waves are radiated from the SAW elements 721, 722 into the additive S so that the liquid additive Sk is emitted in a spray state.

As the mode using a thermal vaporization method, for example, as illustrated in FIG. 15B, a supporting table 731 is disposed in a vaporization chamber 730, and a vaporization plate 732 is disposed on this supporting table 731. Further, for example, a planar heater 733 is disposed in the supporting table 731 directly below the vaporization plate 732, and a temperature sensor 734 for detecting the temperature of the vaporization plate 732 is disposed. In this mode, the control device 80 controls heating of the planar heater 733 based on the temperature information from the temperature sensor 734.

Here, the vaporization plate 732 is made of a corrosion-resistant material having a high thermal conductivity (for example, stainless steel or various types of ceramics including glass). The control device 80 is configured to variably set the target temperature of the planar heater 733 in accordance with the kind of the liquid additive Sk to be dripped. The target temperature of the heater 733 is set to a temperature at which the temperature of the vaporization plate 732 heated by the planar heater 733 becomes equal to or higher than the vaporization temperature of the liquid additive Sk to be dripped.

In this mode, the vaporized additive Sk is sprayed on the filter surface of the cleaning filter 40 through an opening 735 of the vaporization chamber 730.

Note that, the vaporization plate 732 is, for example, fixedly disposed on the supporting table 731, but the configuration of the vaporization plate 732 is not limited thereto. The supporting table 731 may be provided with a movable table so as to be vibrated, thereby further promoting the vaporization of the additive Sk.

Allergenic particles floating in the air, such as mite and mold, cause rhinitis, asthma, and the like, and are contaminants which need to be removed. Allergenic particles are made of protein, and there is an antibody which binds to only a certain protein among innumerable proteins. With use of such property of the antibody, an immunological measuring method using the antibody which recognizes a specific allergenic particle, a so-called enzyme-linked immunorsorbent assay (ELISA) method, has already been practically applied.

With use of this idea, for example, when the air cleaning apparatus employs the cleaning filter 40 including the microorganism removal filter 42 impregnated with a certain antibody, a specific protein, that is, an allergenic particle, can be effectively and selectively trapped. Moreover, when this property is used as an allergenic particle sensor, the allergenic particle concentration in the indoor air can be monitored.

Specifically, when a given quantity of an antibody is applied to the microorganism removal filter 42 formed of a non-woven fabric or the like, the particle removal ability of the microorganism removal filter 42 and the protein binding ability of the antibody are coupled, thereby efficiently removing mites and their feces in the indoor air. That is, through application of a certain type of antibody to the microorganism removal filter 42, the removal rate of the microorganism removal filter 42 for a certain type of allergenic particle is enhanced. Conventionally, a fine filter has been adopted for enhancing the dust collection efficiency, but in such a configuration, the pressure loss of the filter may be increased. However, in this embodiment, even when the microorganism removal filter 42 is not a fine filter, through application of an antibody which reacts with allergenic particles, the trapping performance for allergenic particles can be ensured. Thus, there is less fear that the pressure loss of the filter is increased.

There is a conventional air cleaning apparatus in which a "dust sensor" and a "pollen sensor" are installed, but dust and pollen are identified by the particle size of the measured particle. Accordingly, there arises a problem of uncertainty about the identifiability, but this embodiment can solve this problem. Specifically, as a method of measuring the weight of a protein adhered to the antibody, there can be provided a method for measurement with a SAW method using ultrasonic vibration or the like, or a method including conducting a current through an adhered protein and identifying an adhesion amount based on a level of the conducted current.

Fourth Embodiment

Figure 16:
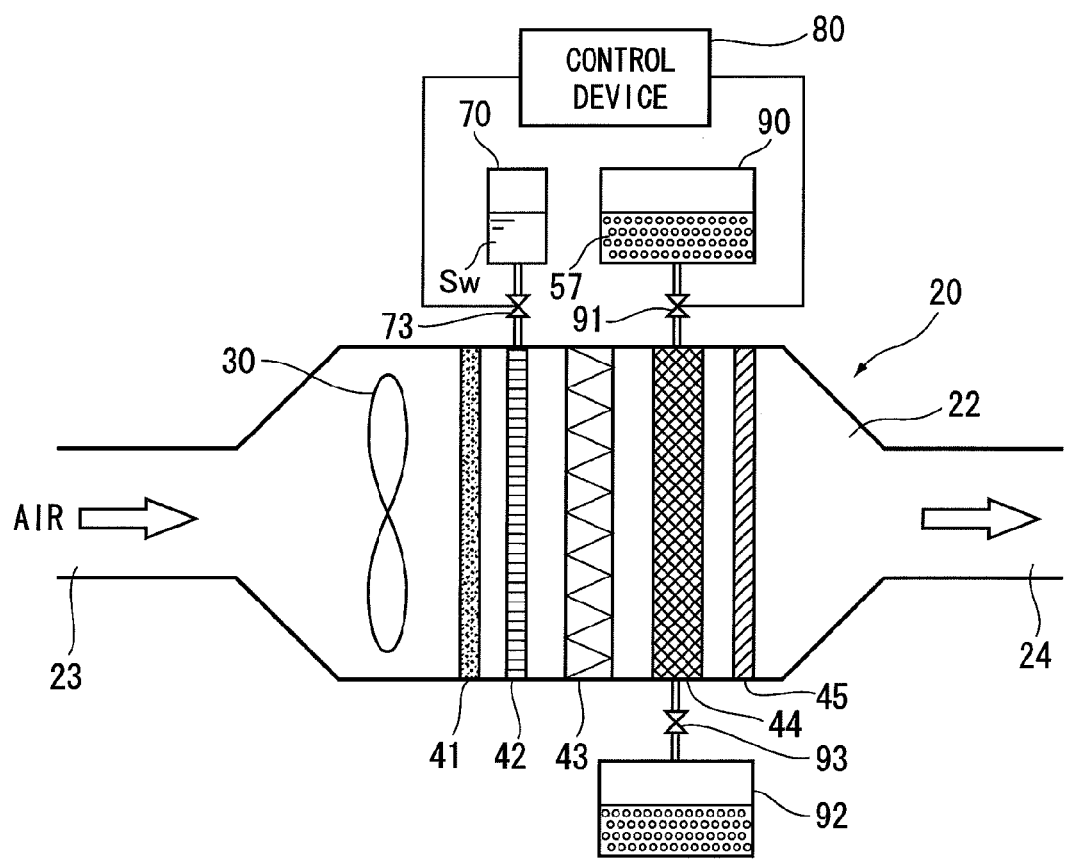
FIG. 16 is an explanatory diagram illustrating a main part of an air cleaning apparatus according to a fourth embodiment of the present invention.

FIG. 16 illustrates a main part of a cleaning filter 40 of an air cleaning apparatus 20 according to a fourth embodiment of the present invention.

In FIG. 16, the basic configuration of the cleaning filter 40 is substantially similar to that of the first embodiment. However, unlike the first embodiment, the adsorbent 57 of the gas removal filter 44 is periodically replenished and discharged.

In FIG. 16, reference symbol 90 represents an adsorbent replenishing bottle; 91, an on-off valve for the adsorbent replenishing bottle 90; 92, an adsorbent discharging bottle; and 93, an on-off valve for the adsorbent discharging bottle 92. The control device 80 periodically controls opening and closing of the on-off valves 91, 93, thereby accomplishing the replenishment and discharge of the adsorbent 57.

In this embodiment, the adsorbent 57 of the gas removal filter 44 is suitably replaced, thereby extending the lifetime of the gas removal filter 44.

Fifth Embodiment

Figure 17A:
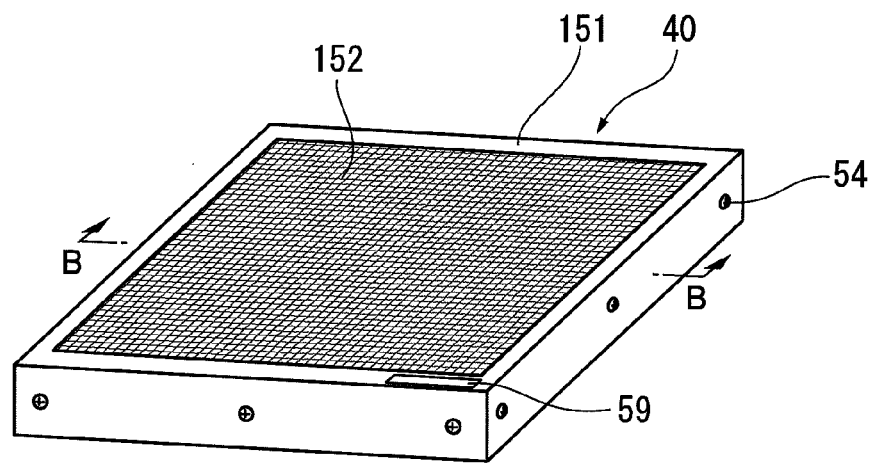
FIG. 17A is an explanatory diagram illustrating a main part of an air cleaning apparatus according to a fifth embodiment of the present invention.
Figure 17B:
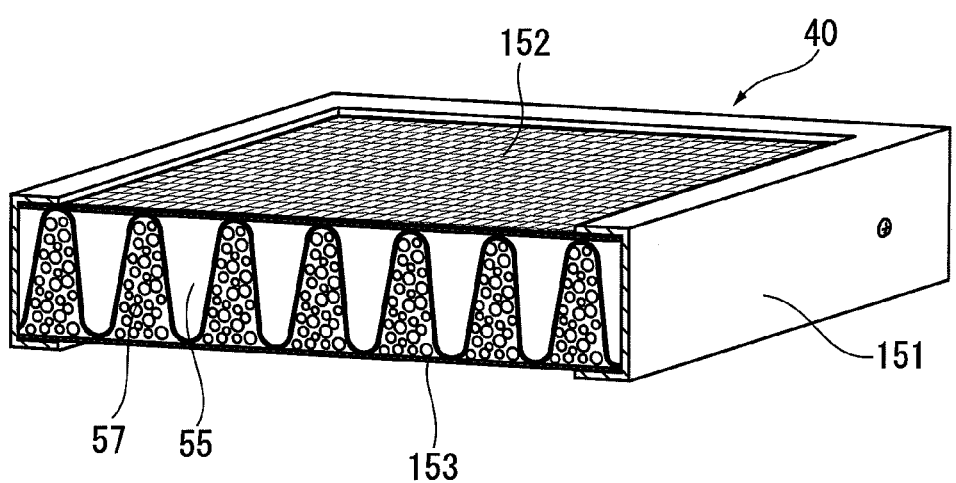
FIG. 17B is an explanatory cross-sectional view cut along the B-B line in FIG. 17A.

FIGS. 17A and 17B illustrate a main part of a cleaning filter 40 according to a fifth embodiment of the present invention.

In FIGS. 17A and 17B, the cleaning filter 40 is provided with openings on both sides of a heat-resistant outer holding frame 151. The openings are provided with, for example, heat-resistant filter elements 152, 153 capable of trapping particulate contaminants, such as microbial particles. The adsorbent 57 capable of trapping gaseous contaminants is filled to be distributed in the outer holding frame 151 by using the plurality of baffle plates 55.

In this embodiment, a single filter unit can trap both gaseous contaminants and particulate contaminants.

Sixth Embodiment

Figure 18A:
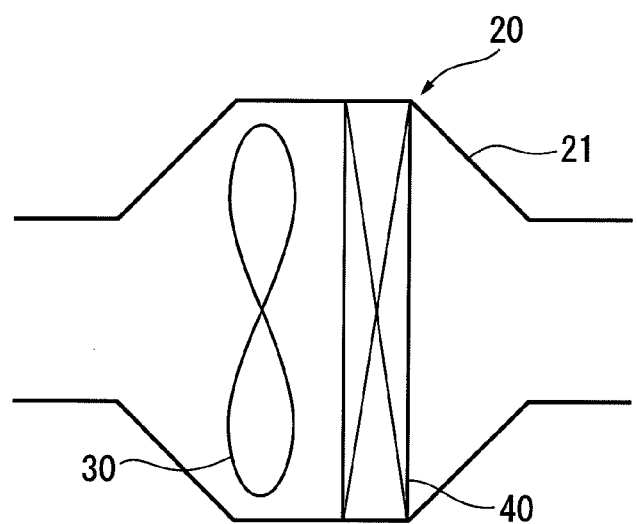
FIG. 18A is an explanatory diagram illustrating a main part of an air cleaning apparatus according to a sixth embodiment of the present invention.
Figure 18B:
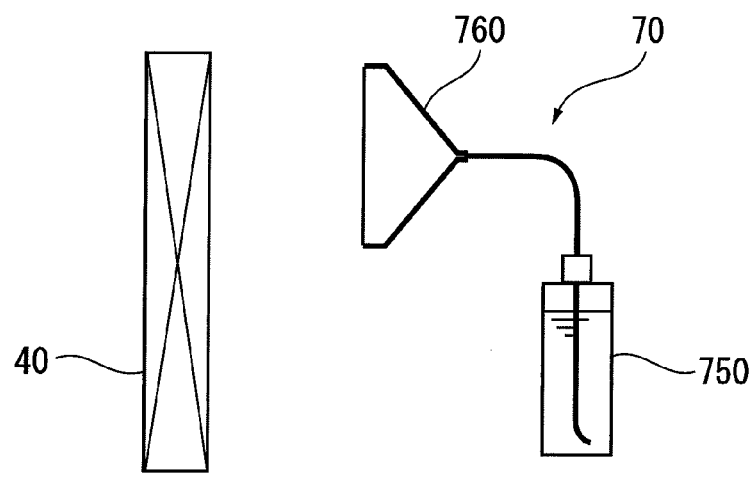
FIG. 18B is an explanatory diagram illustrating an overview of a separate-type additive supply device for recovering performance of the cleaning filter used in this embodiment.

FIGS. 18A and 18B illustrate a main part of an air cleaning apparatus according to a sixth embodiment of the present invention.

In FIG. 18A, the air cleaning apparatus 20 includes the air duct 21 as a cleaning apparatus main body in which the air flow passage 22 is defined and formed. The intake fan 30 and the cleaning filter 40 are disposed in this air duct 21.

In this embodiment, as illustrated in FIG. 18B, the cleaning filter 40 is removably disposed in the air duct 21, and after being removed from the air duct 21, the cleaning filter 40 is supplied with the additive S from a separate-type additive supply device 70 which is disposed as a unit separate from the air cleaning apparatus 20.

Here, in this embodiment, the cleaning filter 40 includes a particle removal filter element and a gas removal filter element.

In this embodiment, as illustrated in FIG. 18B and FIGS. 19A and 19B, the separate-type additive supply device 70 includes an additive bottle 750 for storing a predetermined additive S, and a spray region restricting hood 760 for spraying the additive S in this additive bottle 750 to the surface of the cleaning filter 40 in a substantially rectangular shape.

In this embodiment, the spray region restricting hood 760 includes a hood main body 761 provided with a hollow quadrangular pyramid frame portion 763 formed on one end side of a through rectangular frame portion 762. A spray nozzle 764 is disposed at the center of the quadrangular pyramid frame portion 763 of the hood main body 761. This spray nozzle 764 is connected to a tube 766, which is communicated to the additive bottle 750, via a removable tube connector 765. The rectangular frame portion 762 of the hood main body 761 is provided at its opening edge with a packing 767 for ensuring air-tightness. The rectangular frame portion 762 of the hood main body 761 is provided at its lower portion with an additive recovery pit 768 for recovering an excess liquid additive S which has not been sprayed on the cleaning filter 40. Reference symbol 769 represents a ventilation hole formed in the spray region restricting hood 760. The ventilation hole 769 is effective for promoting the spray process of the additive S by introducing an air flow therethrough during the spray process of the additive S with use of, for example, the intake fan 30 of the air cleaning apparatus 20.

In this embodiment, when the additive S is not sufficiently held in the cleaning filter 40, it is only necessary that the cleaning filter 40 be removed from the air duct 21, and the additive S be supplied by the separate-type additive supply device 70.

In this embodiment, now, for example, there are three additive bottles 750 (750a to 750c). Of the three additive bottles 750, the additive bottle 750a stores an additive Sa for acid gas, the additive bottle 750b stores an additive Sb for basic gas, and the additive bottle 750*c* stores an additive Sc for addressing microorganisms.

One of the right and left halves of the filter surface of the cleaning filter 40 is, for example, an acid gas treatment surface X, and the other is a basic gas treatment surface Y. The entire filter surface is applied with the additive Sc for addressing microorganisms.

Then, in this embodiment, the opening of the spray region restricting hood 760 (corresponding to the opening of the rectangular frame portion 762) is formed into a rectangular shape having a size of about ¼ of that of the filter surface of the cleaning filter 40.

Next, the method of using the separate-type additive supply device 70 is described with reference to FIG. 20.

First, the first additive bottle 750*a* is connected to the spray region restricting hood 760 via the tube 766 to be communicated to each other. The spray region restricting hood 760 of the additive supply device 70 is disposed via the packing 767 in close contact with the upper half of the acid gas processing surface X of the filter surface of the cleaning filter 40, and the additive Sa for acid gas is sprayed. At this time, the spray shape of the additive Sa from the spray nozzle 764 is generally a circular shape, but the additive Sa is sprayed under a state in which the spray region of the additive Sa from the spray nozzle 764 is restricted to the range of the rectangular frame portion 762 of the spray region restricting hood 760.

Next, the spray region restricting hood 760 of the additive supply device 70 is disposed via the packing 767 in close contact with the lower half of the acid gas processing surface X of the filter surface of the cleaning filter 40, and, similarly, the spray process of the additive Sa is performed.

After that, the second additive bottle 750*b* is connected to the spray region restricting hood 760 via the tube 766 so as to be communicated to each other. The spray region restricting hood 760 of the additive supply device 70 is disposed via the packing 767 in close contact with the upper half of the basic gas processing surface Y of the filter surface of the cleaning filter 40, and the additive Sb for basic gas is sprayed. At this time, the additive Sb is sprayed under a state in which the spray region of the additive Sb from the spray nozzle 764 is restricted to the range of the rectangular frame portion 762 of the spray region restricting hood 760.

Next, the spray region restricting hood 760 of the additive supply device 70 is disposed via the packing 767 in close contact with the lower half of the basic gas processing surface Y of the filter surface of the cleaning filter 40, and, similarly, the spray process of the additive Sb is performed.

Finally, the third additive bottle 750*c* is connected to the spray region restricting hood 760 via the tube 766 to be communicated to each other. The spray region restricting hood 760 of the additive supply device 70 is disposed via the packing 767 in close contact with the upper half of the acid gas processing surface X of the filter surface of the cleaning filter 40, and the additive Sc for addressing microorganism is sprayed. At this time, the additive Sc is sprayed under a state in which the spray region of the additive Sc from the spray nozzle 764 is restricted to the range of the rectangular frame portion 762 of the spray region restricting hood 760.

Next, the spray region restricting hood 760 of the additive supply device 70 is disposed via the packing 767 in close contact with the lower half of the acid gas processing surface X, the upper half of the basic gas processing surface Y, and the lower half of the basic gas processing surface Y in the filter surface of the cleaning filter 40, in this order, and, similarly, the spray process of the additive Sc is performed.

Under this state, the additive Sa for acid gas is sprayed on the acid gas processing surface X of the cleaning filter 40, the additive Sb for basic gas is sprayed on the basic gas processing surface Y of the cleaning filter 40, and the additive Sc for addressing microorganisms is sprayed on the entire surfaces X and Y.

As described above, the performance of the cleaning filter 40 is recovered by spraying the additive S thereon. Thus, when the cleaning filter 40 is placed again in the air duct 21, the cleaning function of the cleaning filter 40 of the air cleaning apparatus 20 can be satisfactorily ensured again.

Figure 21A:
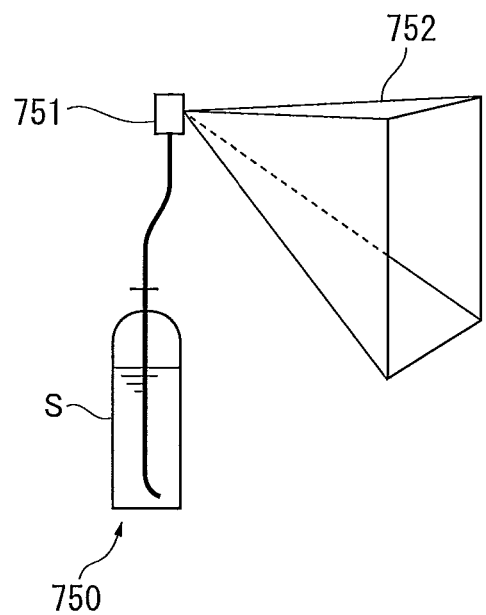
FIGS. 21A and 21B are explanatory diagrams illustrating modified modes of the separate-type additive supply device used in the sixth embodiment.

In this embodiment, the additive supply device 70 uses the spray region restricting hood 760, but the present invention is not limited thereto. For example, as illustrated in FIG. 21A, a spray nozzle 751 may be disposed on the additive bottle 750, and a spray region restricting guide 752 may be additionally disposed on this spray nozzle 751. This spray region restricting guide 752 is formed into a hollow quadrangular pyramid shape which widens as the distance from the spray nozzle 751 increases so as to restrict the spray region of the additive S sprayed from the spray nozzle 751 to a rectangular shape. The spray region restricting guide 752 has a function substantially similar to that of the spray region restricting hood 760.

Figure 21B:
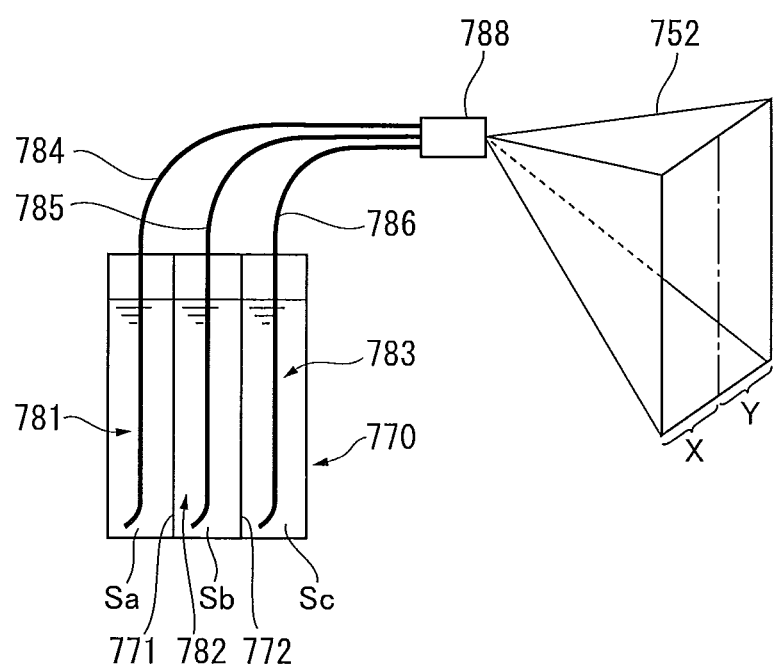

In this embodiment, the additive bottles 750 are separately disposed for the respective additives S, but the present invention is not limited thereto. For example, as illustrated in FIG. 21B, the inside of a single additive container 770 may be divided by a plurality of partitions 771, 772 into a plurality of additive chambers 781, 782, 783, which respectively store the corresponding additives S (Sa, Sb, Sc). A division spray nozzle 788 is communicated to the respective chambers 781 to 783 of the additive container 770 via tubes 784 to 786, respectively, which are connected to the division spray nozzle 788 in a divided manner. The spray region restricting guide 752 is additionally disposed on this division spray nozzle 788.

In this embodiment, the respective additives S only need to be separately sprayed by the division spray nozzle 788 on the filter surface of the cleaning filter 40.

Note that, in this embodiment, the cleaning filter 40 is removed from the air duct 21, but the present invention is not limited thereto. The additives S may be supplied by the separate-type additive supply device 70 on the filter surface of the cleaning filter 40 under a state in which the filter surface is exposed outside the air duct 21.

Seventh Embodiment

Figure 22A:
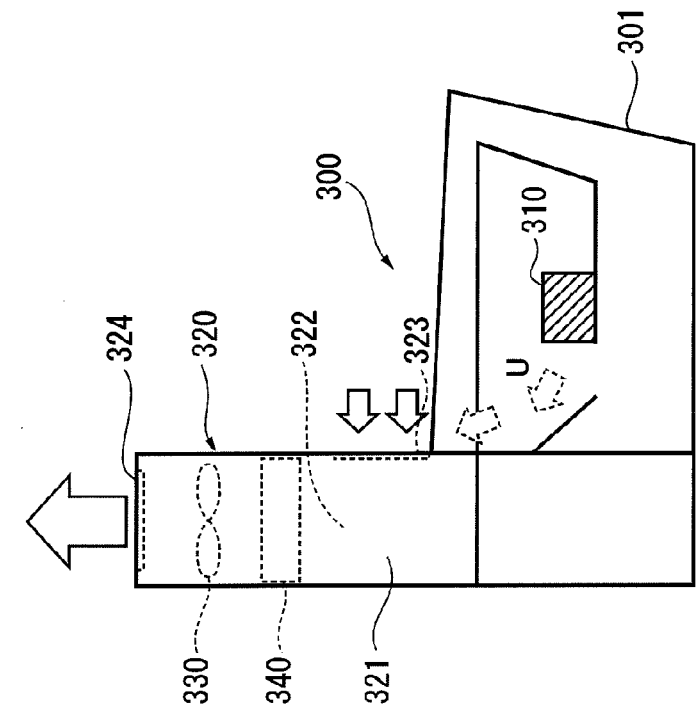
FIG. 22A is an explanatory perspective view illustrating a main part of an air cleaning apparatus according to a seventh embodiment of the present invention, which is used for a toilet unit.
Figure 22B:
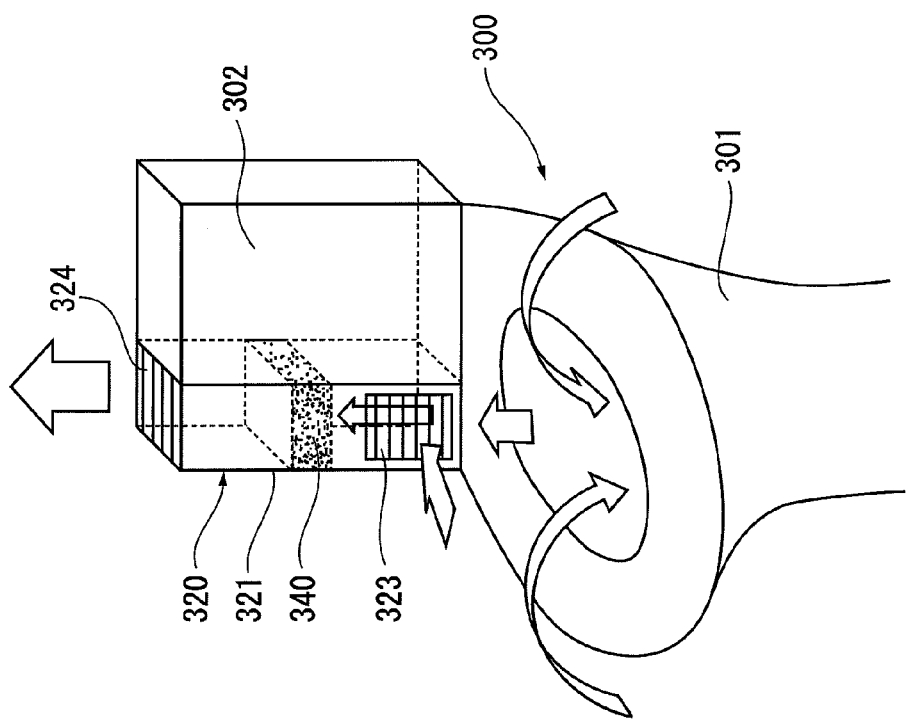
FIG. 22B is an explanatory side view of the air cleaning apparatus.

FIGS. 22A and 22B illustrate an example in which an air cleaning apparatus according to a seventh embodiment of the present invention is incorporated into a toilet unit.

In FIGS. 22A and 22B, a toilet unit 300 includes a toilet unit main body 301 including a seat portion, a tank 302 disposed behind the toilet unit main body 301, for storing cleaning water, and an air cleaning apparatus 320 disposed behind the above-mentioned toilet unit main body 301 and laterally adjacent to the above-mentioned tank 302.

In this embodiment, the air cleaning apparatus 320 includes an air duct 321 in which an air flow passage 322 is formed therein. An inlet opening 323 and an outlet opening 324 of this air duct 321 are respectively provided with louvers. A cleaning filter 340 is removably mounted in the middle of the air duct 321. An air flow is generated in the air flow passage 322 by an intake fan 330 disposed in the air duct 322.

In this embodiment, the cleaning filter 340 includes a dust removal filter for removing dust and the like in the surrounding environment space of the toilet unit 300, and a gas removal filter for removing gas, such as odor U generated from human waste 310, odor remaining in the toilet unit 300, and odor in the surrounding environment space of the toilet unit. In particular, for example, a gas removal filter having a configuration substantially similar to that of the gas removal filter 44 of the regeneration cartridge configuration of the first embodiment is used. In view of providing the deodorization effect, the gas removal filter is preferably configured to collect gas generated from human excreta or the like by a trapping material such as active carbon and Tenax.

According to this embodiment, when water is saved in the toilet unit 300, various kinds of odor including the odor U generated from the human waste 310 remain around the toilet unit 300, but the air cleaning apparatus 320 of this embodiment removes the odor around the toilet unit 300 by the gas removal filter of the cleaning filter 340.

In this embodiment, the gas removal filter of the cleaning filter 340 is configured as a regeneration cartridge, and hence the gas removal filter can be reused after being regenerated by the filter regeneration device 110 similar to that of the first embodiment (for example, the thermal desorption device 111).

Eighth Embodiment

Figure 23:
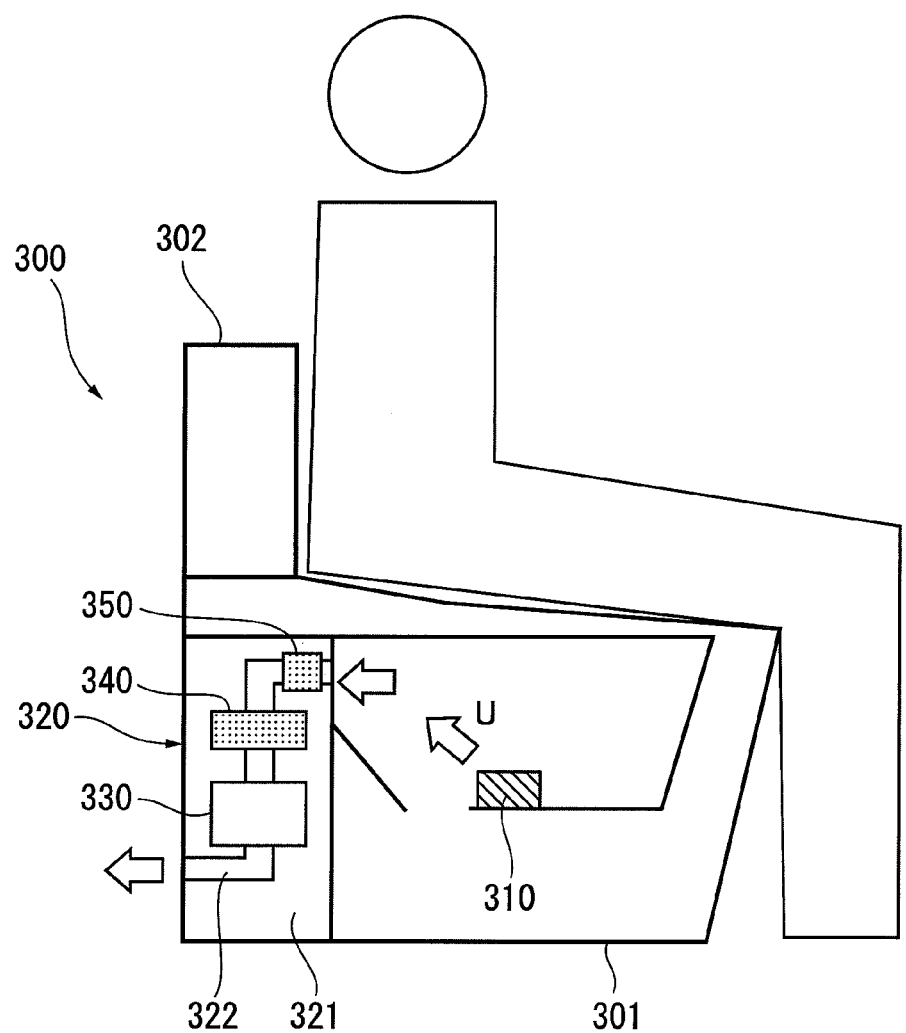
FIG. 23 is an explanatory diagram illustrating a main part of an air cleaning apparatus according to an eighth embodiment of the present invention, which is used for a toilet unit.

FIG. 23 illustrates an example in which an air cleaning apparatus according to an eighth embodiment of the present invention is incorporated into a toilet unit.

In FIG. 23, similarly to the seventh embodiment, the toilet unit 300 includes the toilet unit main body 301 including a seat portion, the tank 302 disposed behind the toilet unit main body 301, for storing cleaning water, and an air cleaning apparatus 320 disposed behind the above-mentioned toilet unit main body 301 and adjacent to a lower portion of the above-mentioned tank 302.

In this embodiment, the basic configuration of the air cleaning apparatus 320 is substantially similar to that of the seventh embodiment, but, unlike the seventh embodiment, there is additionally provided a diagnosis element which enables a plurality of toilet users to simultaneously take health examinations. Components similar to those of the seventh embodiment are represented by similar reference symbols, and detailed descriptions thereof are omitted here.

Figure 24A:
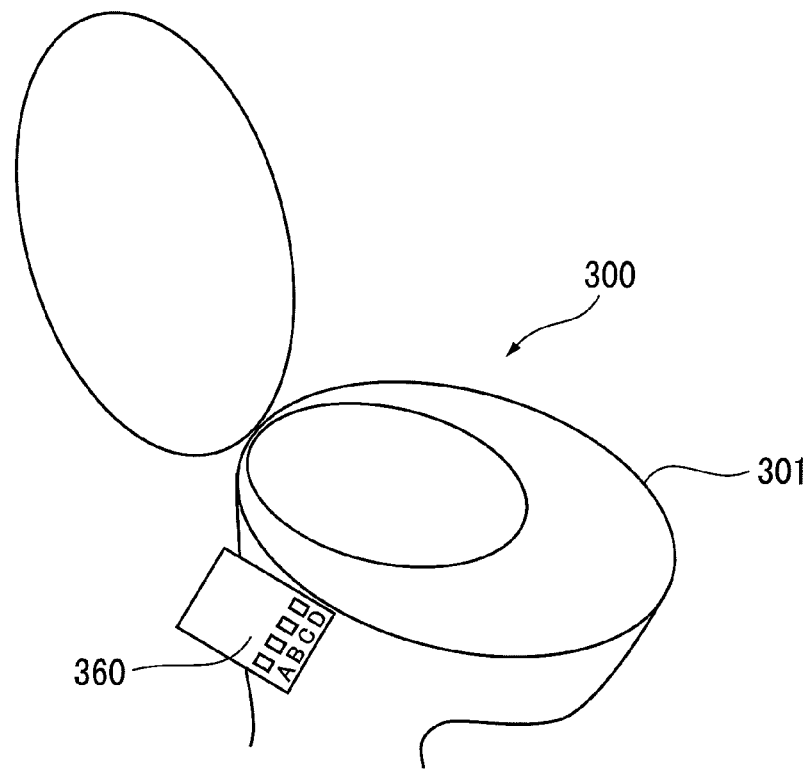
FIG. 24A is an explanatory diagram illustrating a selective operation example of individual cartridges used in the eighth embodiment.
Figure 24B:
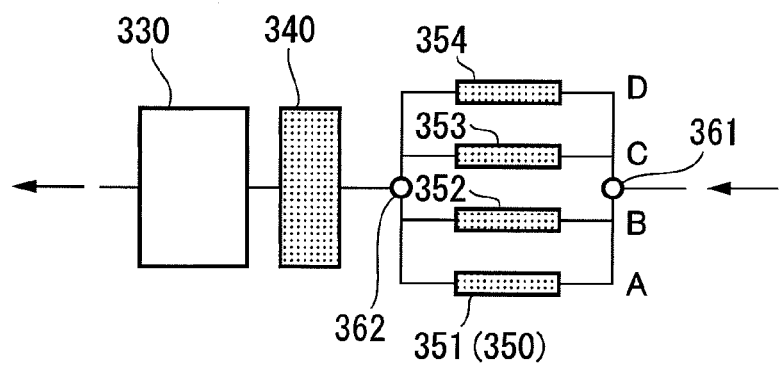
FIG. 24B is an explanatory diagram illustrating an example of a switching selection system for the individual cartridges.

Here, as the diagnosis element, as illustrated in FIG. 23 and FIGS. 24A and 24B, a plurality of gaseous substance collecting tubes 350 (specifically, 351 to 354) are disposed in the air flow passage 322 of the air duct 321. These gaseous substance collecting tubes 350 (351 to 354) can be selectively switched via switching valves 361, 362. There is adopted a method in which, through selection of the gaseous substance collecting tube 350 (for example, 351) corresponding to any one of toilet users A to D, the odor (gaseous substance) generated from the toilet user (for example, A) is collected.

As illustrated in FIG. 24A, on the side portion of the toilet unit main body 301, a user selection switch 360 for selecting a toilet user is disposed. When the toilet user operates the above-mentioned user selection switch for identification, the above-mentioned switching valves 361, 362 are suitably switched in accordance with an operation signal from this user selection switch 360.

Moreover, gaseous substances, dusts, and the like, which have passed through the gaseous substance collecting tube 350, are effectively removed by the cleaning filter 340 disposed on the downstream side of the air flow passage 322.

Note that, the position where the gaseous substance collecting tube 350 is disposed is not limited to the air flow passage 322 in the air duct 321 as long as the gaseous substances can be collected. A hot water wash nozzle, the edge of the toilet unit 300, or a toilet seat portion may be suitably selected.

In this embodiment, similarly to the seventh embodiment, for example, the gas removal filter of the cleaning filter 340 is configured as a regeneration cartridge, and hence the gas removal filter can be reused through a regeneration process by the filter regeneration device 110. For example, collected gas can be separated through a process such as thermal desorption so that active carbon as the trapping material is regenerated. Moreover, desorbed gas can be analyzed so that health information of the toilet user is collected from biological gas contained in human excreta.

Figure 25A:
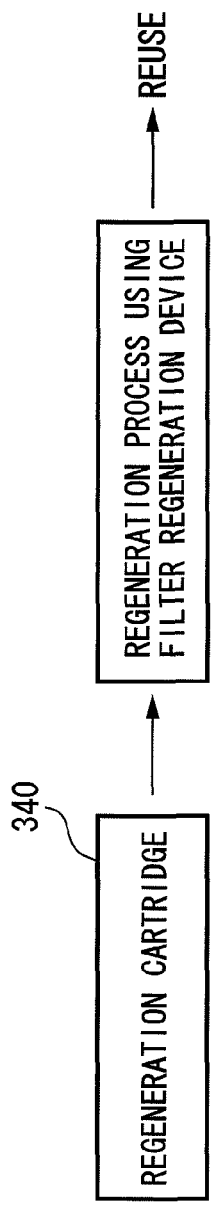
FIG. 25A is an explanatory diagram illustrating an example of a post-process for a regeneration cartridge used in the eighth embodiment.
Figure 25B:
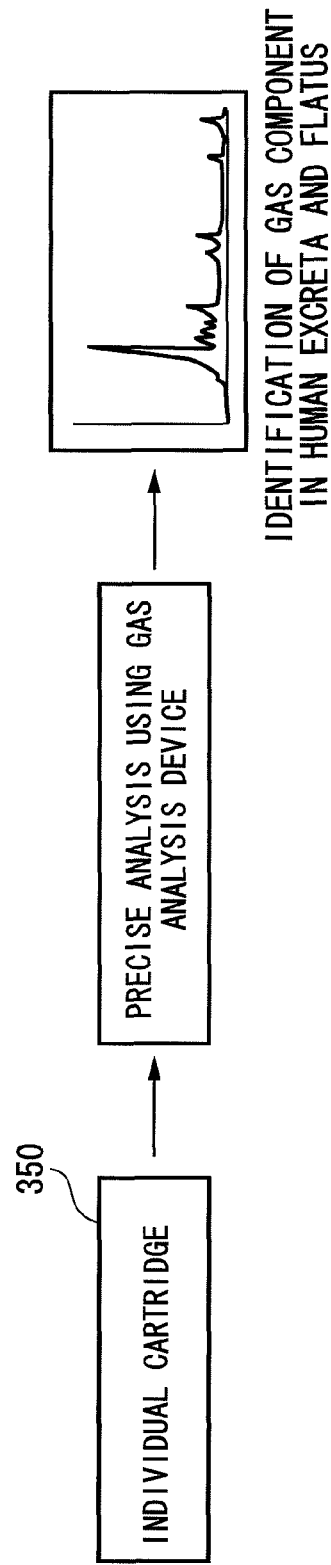
FIG. 25B is an explanatory diagram illustrating an example of a post-process for an individual cartridge used in the eighth embodiment.

In this embodiment, the plurality of gaseous substance trapping tubes 350 are disposed as individual cartridges for the respective toilet users, and hence, as illustrated in FIG. 25B, for example, generated gaseous substances for the respective toilet users are periodically collected by the gaseous substance trapping tubes 350 (351 to 354) as the individual cartridges, and are precisely analyzed by an analysis device, such as a gas chromatograph mass spectrometer (GC/MS), an ion chromatograph (IC), and a high performance liquid chromatograph (HPLC). Accordingly, a qualitative analysis and a quantitative analysis of generated substances can be performed.

As described above, in this embodiment, based on the analysis information, health information related to excretion of the toilet users can be periodically collected so that differences from others and changes with time can be revealed and comparison with information obtained from previous research findings can be performed. With this, the health conditions of the toilet users can also be diagnosed.

For example, it is known that some of the gaseous substances generated from human excreta are related to specific diseases.

ammonia: liver disease methyl sulfide: hepatic coma trimethylamine (amines): uremia acetone (alcohols): type I diabetes mellitus Therefore, when the amount of a specific gaseous substance is extremely large, it is easily predicted that there is a suspicion of a disease related to the specific gaseous substance.

With this, the toilet users can examine and manage their individual health.

In this embodiment, the gaseous substance collecting tubes 350 are disposed for the respective toilet users, but the present invention is not limited thereto. For example, various types of sensors (for kind and quantity of generated gas, excretion quantity, lightness/chromaticity/chroma, and the like) may be disposed in the toilet unit 300. Information on the kind and concentration of a generated substance, excretion quantity, the color of excretion, and the like, is collected by the various types of sensors in real time, and the collected data may be used as a health examination material of the toilet users. For example, in a memory of a control device in the toilet unit 300, the collected information is stored to be recognized with respect to 1) ID, 2) excretion time, 3) excretion quantity, 4) color-related information, and 5) others, and may be used at the time of a health examination.

This configuration is preferred in that the health condition over a long period of time can be grasped by continuously measuring, with use of the sensors, information on human excreta at the toilet unit.

Ninth Embodiment

Figure 26:
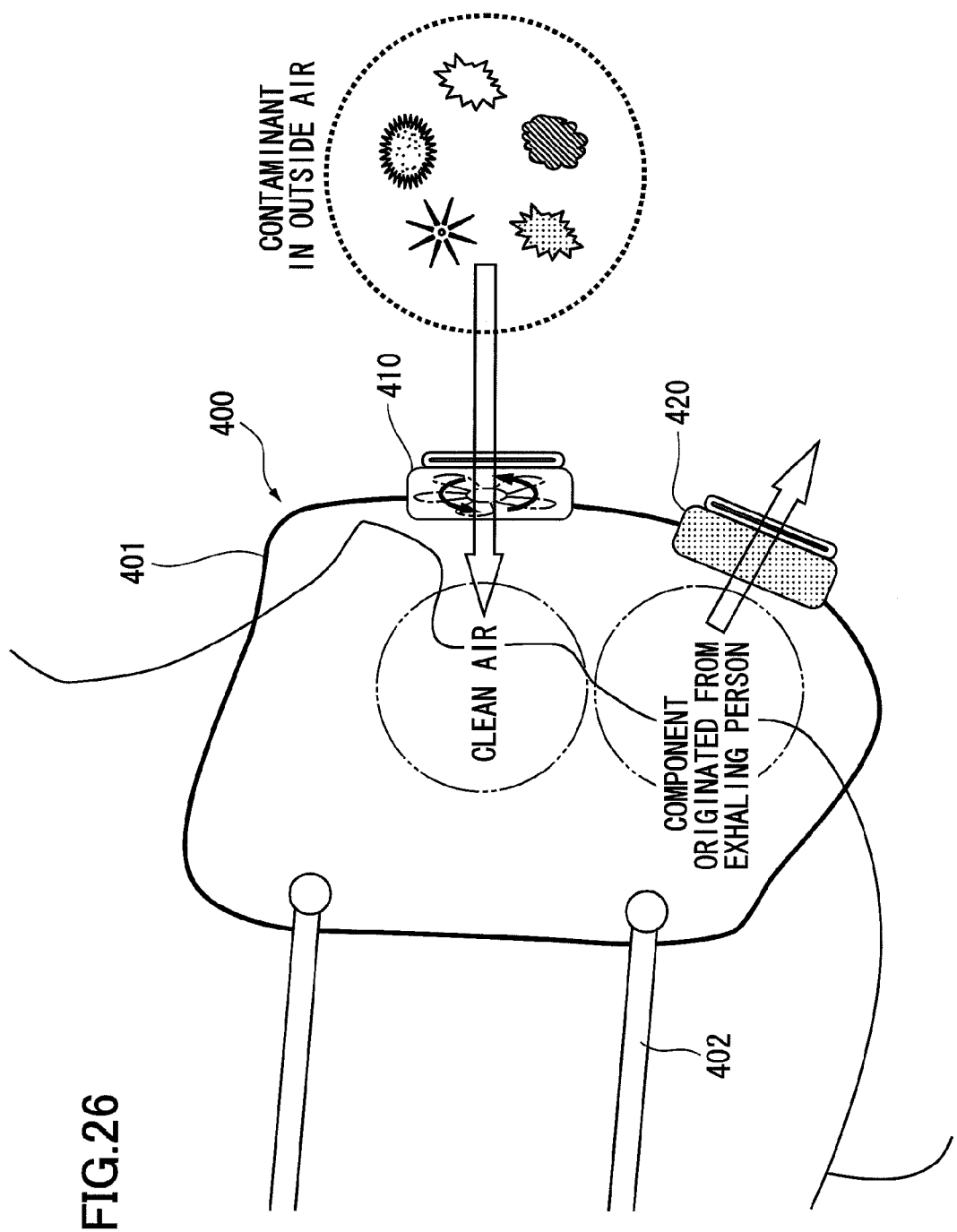
FIG. 26 is an explanatory diagram illustrating a main part of a mask as an air cleaning apparatus according to a ninth embodiment of the present invention.

FIG. 26 illustrates a mask as an air cleaning apparatus according to a ninth embodiment of the present invention.

Generally, a mask can be considered to be an example of an air cleaning apparatus in a broad sense in terms of the fact that inspired air is taken-in while removing contaminants in the outside air, or expired air is released while removing contaminants therein.

A mask 400 according to this embodiment is configured to take-in cleaned outside air, and contaminants in expired air are examined so as to enable disease diagnosis. The mask 400 includes a mask main body 401, an attaching fixture 402 for attaching the mask 400, an inspiration filter 410 disposed on the mask main body 401 in the vicinity of the nostril, for cleaning inspired air, and an expiration filter 420 disposed on the mask main body 401 in the vicinity of the mouth, for cleaning and releasing expired air.

In this embodiment, the mask main body 401 is formed into a cup shape for enabling the gap between the face of a user and the mask to be narrowed with high accuracy so that the air tightness with the face is ensured.

Figure 27A:
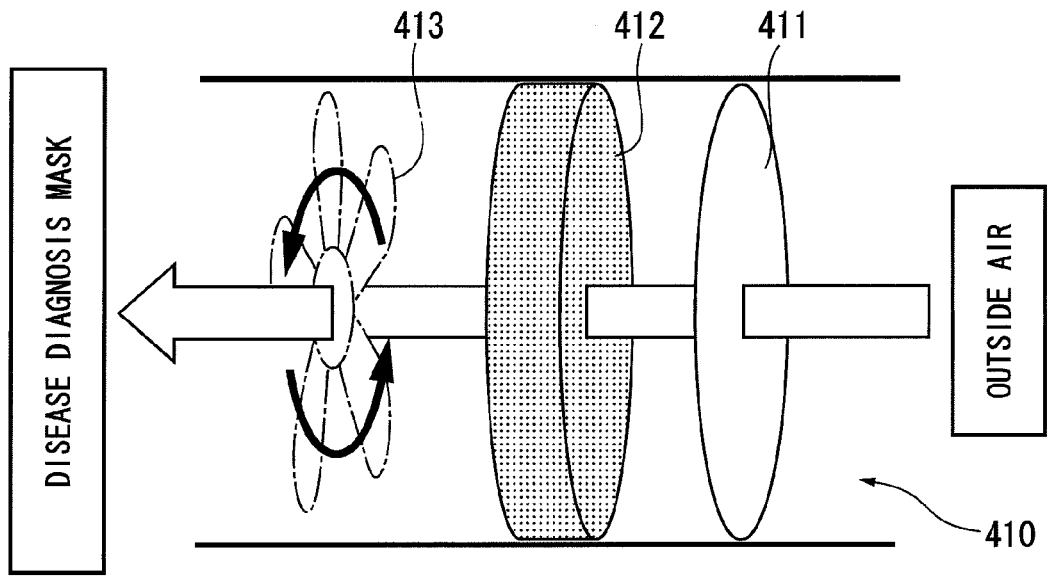
FIG. 27A is an explanatory diagram illustrating a configuration example of an inspiration filter used in the mask according to the ninth embodiment.

As illustrated in FIG. 26 and FIG. 27A, the inspiration filter 410 includes a dust removal filter 411 and a gas removal filter 412 in this order from the outside air side, so as to remove contaminants in the outside air.

In particular, in this embodiment, the gas removal filter 412 is configured as a regeneration cartridge holding a trapping material, such as active carbon.

In order to reduce respiratory load when wearing the mask 400, an intake fan 413 is disposed in the inspired air passage of the inspiration filter 410. The intake fan 413 is adjusted so that supply air is forcedly introduced in a quantity equal to the respiratory quantity of the mask wearer and thus the respiration of the mask wearer becomes substantially the same as that in a normal state.

Figure 27B:
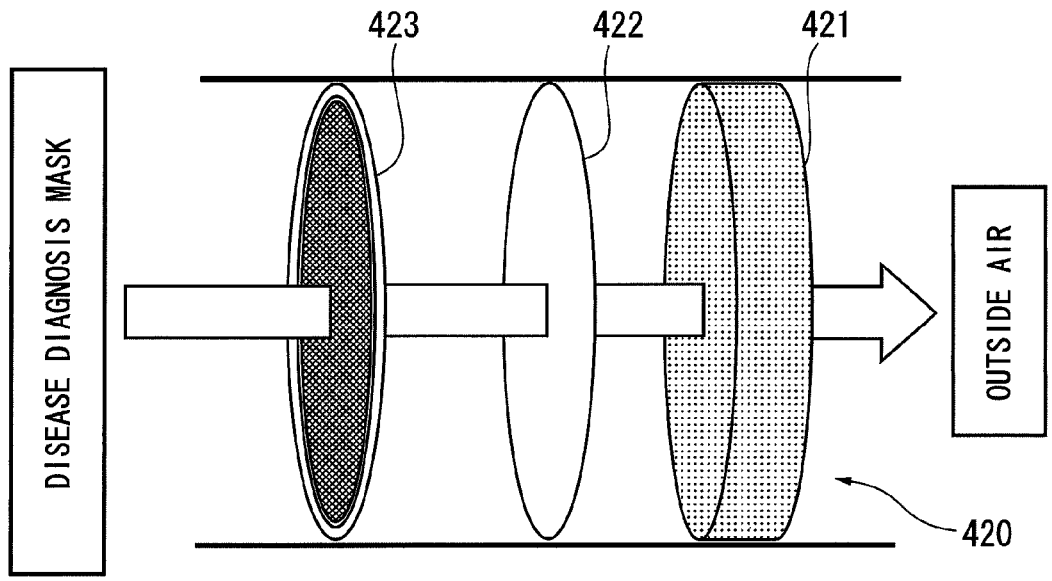
FIG. 27B is an explanatory diagram illustrating a configuration example of an expiration filter used in the mask according to the ninth embodiment.

On the other hand, as illustrated in FIG. 26 and FIG. 27B, the expiration filter 420 includes, from the outside air side of the mask main body 401, a collecting filter 421 for collecting contaminants in expired air, a non-woven fabric filter 422 on the inner side of the collecting filter 421, and a check valve 423 on the inner side of the non-woven fabric filter 422, for preventing the outside air from entering.

Here, the collecting filter 421 is made of active carbon, zeolite, silica gel impregnated with 2,4-dinitrophenylhydrazine (DNPH), non-woven fabric, or the like, and configured as a regeneration cartridge removably mounted to the mask main body 401.

The non-woven fabric filter 422 is applied with a chemical solution for removing dust and specific contaminants in advance.

Moreover, the check valve 423 is configured to prevent reverse flow of outside air so that the outside air cannot enter the collecting filter 421, and thus only the components originated from the exhaling person as the mask user are collected in the collecting filter 421.

Next, the function of the mask according to this embodiment is described.

According to this embodiment, the mask 400 includes the inspiration filter 410 (the dust removal filter 411, the gas removal filter 412). Moreover, the check valve 423 is disposed in the portion of the collecting filter 421 of the expiration filter 420. Accordingly, components in the outside air cannot pass through the collecting filter 421 so that components collected in the collecting filter 421 are limited to those originated from the expired air of the mask user.

Moreover, components in the expired air are widely different among the mask users so that the kind and concentration of the components are hard to estimate. Accordingly, it is desired that the mask wearing time be long enough for causing as large an amount of expired air as possible to pass through the collecting filter 421 and for trapping contaminants in the expired air. However, the pressure loss due to the expiration filter 420 including the collecting filter 421 for trapping contaminants in the expired air may impose a burden on the mask user with respect to respiration. Accordingly, it may be impossible to measure contaminants in the air expired under a normal state. In this regard, this embodiment adopts a forced air intake method in the intake fan 413 so that an excess burden on the mask user with respect to respiration can be effectively avoided.

That is, in this embodiment, clean air is sent into the mask 400 by the intake fan 413 disposed in front of the nostril so that the inside of the mask 400 is constantly maintained in a positive pressure. With this, the mask user inhales clean air which is constantly supplied into the mask 400, and contaminants in the expired air are caused to pass through the collecting filter 421 disposed in front of the mouth so as to be trapped therein.

Here, when the contaminants trapped in the collecting filter 421 are gaseous substances, through the regeneration process by the filter regeneration device, for example, the process such as thermal desorption and solvent extraction, the contaminants are separated from the collecting filter 421 and analyzed by an analysis device, such as a gas chromatograph mass spectrometer (GC/MS), a gas chromatograph (GC), a high performance liquid chromatograph (HPLC), and an ion chromatograph (IC), so as to perform a qualitative analysis and a quantitative analysis.

When the contaminants collected in the collecting filter 421 are microbial particles, such as bacteria, fungi, and viruses, the contaminants can be separated from the collecting filter 421 by an operation, such as washing, and identified by solution emission, microscopic observation, or the like.

With this, disease and health information can be obtained from the expired air of the mask user.

Note that, when the gas removal filter 412 of the inspiration filter 410 is regenerated, through an analysis of gaseous contaminants collected by the gas removal filter 412, information on air pollution in the environment where respiration is performed can be obtained.

EXAMPLE

Example 1

In this example, the air cleaning apparatus was disposed in an environment control-type large chamber (air volume: 4.98 $[m^3]$), and the apparatus performance was obtained by measuring concentrations on the upstream and downstream sides of the air cleaning apparatus. The inside of the chamber was controlled under a fixed environmental condition (temperature: 28±1 [° C.], relative humidity: 50±1 [%], ventilation frequency: 0.03±0.003 [1/h]), and clean air was constantly supplied.

Figures 28A, 28B:
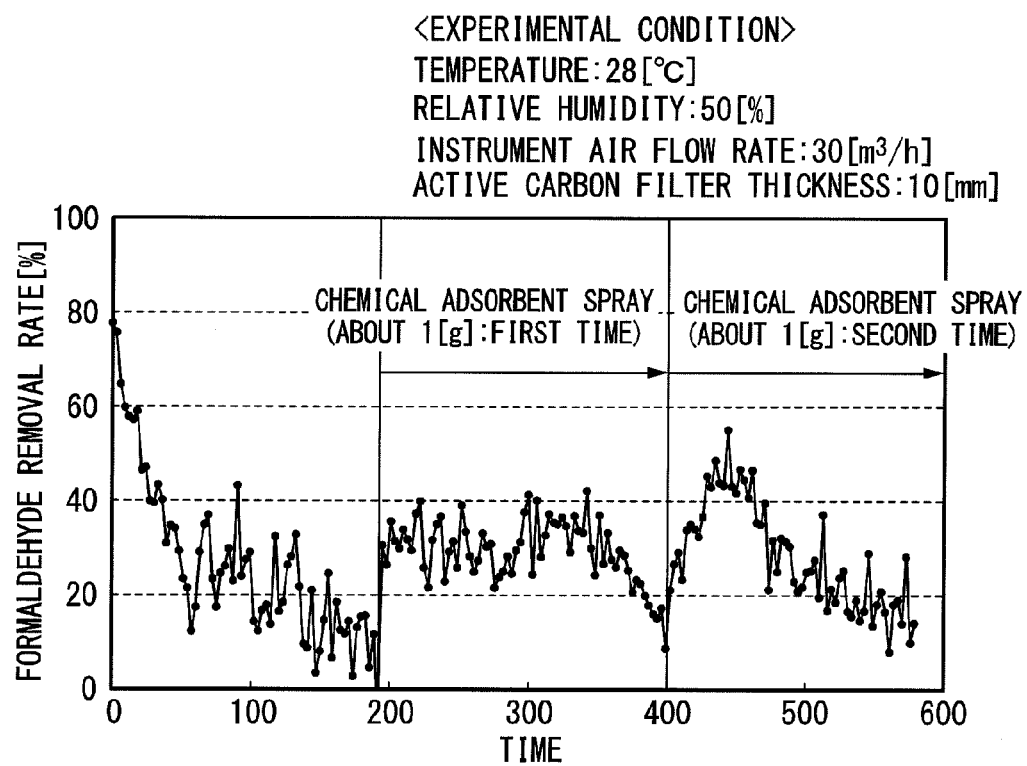
FIG. 28A is a graph showing a removal rate change of formaldehyde as a gaseous contaminant when a spray experiment was conducted for a chemical adsorbent using a cleaning filter according to Example 1.
FIG. 28B is an explanatory diagram illustrating a computational expression of the contaminant removal rate of FIG. 28A.

The results are shown in FIG. 28A.

The computational expression of the contaminant removal rate that is used in this case is illustrated in FIG. 28B.

The actually measured value of the concentration in the chamber was substituted into the computational expression of the removal rate so as to calculate the removal of formaldehyde by the air cleaning apparatus. As a result, as shown in FIG. 28A, the removal rates of formaldehyde were as follows:

initial value: 77.6 [%]; after first spray: 30.5 [%]; after second spray: 55.1 [%].

It was found that the formaldehyde removal performance was greatly recovered by spraying 1 [g] of a chemical adsorbent. In this apparatus, it is considered that the recoverability is enhanced with further increase of the spray amount.

REFERENCE SIGNS LIST

1 . . . air cleaning apparatus, 2 . . . cleaning apparatus main body, 3 . . . air flow passage, 4 . . . cleaning filter, 5 . . . particle trapping member, 6 . . . gas trapping member, 7 (7a to 7c) . . . trapping material, 8 . . . trapping material holding member, 10 (10a to 10b) . . . trapping material supply device, 15 . . . filter regeneration device.

The invention claimed is:

1. A cleaning filter, which is disposed in an air flow passage of a cleaning apparatus main body of an air cleaning apparatus, for cleaning an air passing through the air flow passage, the cleaning filter comprising:
a gas trapping member for trapping a gaseous contaminant; and
a particle trapping member for trapping a particulate contaminant,
wherein the particle trapping member comprises:
a trapping material comprising liquid additive for trapping a predetermined contaminant selected among contaminants in the air;
a trapping material holding member, which is removably mounted on the cleaning apparatus main body, for holding the trapping material so as to be opposed to the air flow passage with an air permeability ensured; and
a trapping material supply device for supplying the trapping material to the trapping material holding member,
wherein the trapping material holding member is configured as a regeneration cartridge which is subjected to, when removed from the cleaning apparatus main body, a regeneration process including a thermal desorption process for regenerating trapping performance of the trapping material for the predetermined contaminant,
wherein the trapping material holding member configured as the regeneration cartridge has a heat resistance on condition the regeneration process including a thermal desorption process and holds the trapping material eliminated by heat at least on condition the regeneration process including a thermal desorption process,
wherein the regeneration cartridge is subjected to the regeneration process including the thermal desorption process under a state in which the regeneration cartridge holds the trapping material,
wherein the trapping material held by the regeneration cartridge and the predetermined contaminant trapped to the trapping material is eliminated by the regeneration process including a thermal desorption process, and
wherein the trapping material supply device supplies the trapping material to the regeneration cartridge, when the regeneration cartridge after the regeneration process is mounted again on the cleaning apparatus main body.

2. A cleaning filter according to claim 1,
wherein the gas trapping member comprises:
a trapping material comprises liquid additive for trapping a predetermined contaminant selected among contaminants in the air;
a trapping material holding member, which is removably mounted on the cleaning apparatus main body, for holding the trapping material so as to be opposed to the air flow passage with an air permeability ensured; and
a trapping material supply device for supplying the trapping material to the trapping material holding member,
wherein the trapping material holding member is configured as a regeneration cartridge which is subjected to, when removed from the cleaning apparatus main body, a regeneration process including a thermal desorption process for regenerating trapping performance of the trapping material for the predetermined contaminant,
wherein the trapping material holding member configured as the regeneration cartridge has a heat resistance on condition the regeneration process including a thermal desorption process and holds the trapping material eliminated by heat at least on condition the regeneration process including a thermal desorption process and the trapping material having a heat resistance at least on condition of the regeneration process including a thermal desorption process,
wherein the regeneration cartridge is subjected to the regeneration process including the thermal desorption process under a state in which the regeneration cartridge holds the trapping material,
wherein the trapping material held by the regeneration cartridge and the predetermined contaminant trapped to the trapping material is eliminated by the regeneration process including a thermal desorption process,
wherein the trapping material having a heat resistance is regenerated by the regeneration process including a thermal desorption process, and
wherein the trapping material supply device supplies the trapping material to the re regeneration cartridge, when the regeneration cartridge after the regeneration process is mounted again on the cleaning apparatus main body.

3. A cleaning filter according to claim 1, wherein the trapping material holding member comprises:
an outer holding frame having an air permeability; and
a plurality of baffle plates contained in the outer holding frame, in which a solid trapping material is filled to be distributed with an air permeability ensured.

4. A cleaning filter according to claim 2, wherein the trapping material holding member of the particle trapping member comprises a plurality of mesh layers each having a different air permeability and made of a material having a heat resistance, the plurality of mesh layers holding an additive as the trapping material.

5. A cleaning filter according to claim 1, wherein the trapping material holding member of the particle trapping member comprises a plurality of mesh layers each having a different air permeability and made of a material having a heat resistance, the plurality of mesh layers holding an additive as the trapping material.

6. A cleaning filter according to claim 1, wherein the trapping material holding member of the gas trapping member holds the trapping material for trapping a predetermined gaseous contaminant, and further holds a catalyst particle capable of decomposing the predetermined gaseous contaminant, the catalyst particle being provided upstream of the trapping material in an air flowing direction.

7. An air cleaning filter according to claim 1, wherein the trapping material holding member configured as the regeneration cartridge is put in environment of temperature of about 200° C. to 500° C. on condition the regeneration process including a thermal desorption process.

8. An air cleaning filter according to claim 1, wherein the particle trapping member intends to trap microbial particles or allergenic particles as particulate contaminant.

9. An air cleaning apparatus, comprising:

a cleaning apparatus main body in which an air flow passage is formed; and the cleaning filter according to claim 1, the cleaning filter being disposed in the air flow passage of the cleaning apparatus main body.

10. An air cleaning apparatus, comprising:

a cleaning apparatus main body in which an air flow passage is formed; and the cleaning filter according to claim 6, the cleaning filter being disposed in the air flow passage of the cleaning apparatus main body, wherein the cleaning filter or the cleaning apparatus main body comprises heating means capable of heating the catalyst particle.

11. An air cleaning maintenance system, comprising:

the air cleaning apparatus according to claim 9; and a filter regeneration device for regenerating the cleaning filter removed from the air cleaning apparatus, wherein the regenerated cleaning filter is reused.

12. An air cleaning maintenance system according to claim 11, wherein the filter regeneration device puts the trapping material holding member configured as the regeneration cartridge in environment of temperature about 200° C. to 500° C. on condition the regeneration process including a thermal desorption process.

* * * * *